(12) United States Patent
Gray et al.

(10) Patent No.: US 9,849,232 B2
(45) Date of Patent: Dec. 26, 2017

(54) MEDICAL DEVICE MANAGEMENT USING SAFETY SUPERVISOR

(71) Applicant: Ivenix, Inc., Amesbury, MA (US)

(72) Inventors: George W. Gray, North Andover, MA (US); William C. McQuaid, Melrose, MA (US); Remi Depommier, Haverhill, MA (US); Jesse E. Ambrosina, Topsfield, MA (US)

(73) Assignee: Invenix, Inc., Amesbury, MA (US)

( * ) Notice: Subject to any disclaimer, the term of this patent is extended or adjusted under 35 U.S.C. 154(b) by 444 days.

(21) Appl. No.: 14/494,803

(22) Filed: Sep. 24, 2014

(65) Prior Publication Data
US 2015/0088094 A1 Mar. 26, 2015

Related U.S. Application Data

(60) Provisional application No. 61/882,818, filed on Sep. 26, 2013.

(51) Int. Cl.
| | |
|---|---|
| *A61M 5/168* | (2006.01) |
| *A61M 5/142* | (2006.01) |
| *A61M 5/14* | (2006.01) |
| *G06F 19/00* | (2011.01) |

(52) U.S. Cl.
CPC .......... *A61M 5/142* (2013.01); *A61M 5/1407* (2013.01); *G06F 19/3468* (2013.01); *A61M 2205/3584* (2013.01); *A61M 2205/502* (2013.01); *G06F 19/3406* (2013.01)

(58) Field of Classification Search
CPC ............... A61M 5/142; A61M 5/1407; A61M 2205/3584; A61M 2205/502
See application file for complete search history.

(56) References Cited

U.S. PATENT DOCUMENTS

| | | | |
|---|---|---|---|
| 5,800,387 A * | 9/1998 | Duffy | A61M 5/142 604/505 |
| 6,029,083 A | 2/2000 | Flower et al. | |
| 8,034,019 B2 | 10/2011 | Nair et al. | |
| 2003/0159741 A1* | 8/2003 | Sparks | A61M 5/16827 137/814 |
| 2005/0094483 A1* | 5/2005 | Demers | A61L 2/0088 366/142 |
| 2005/0096583 A1* | 5/2005 | Demers | A61M 5/162 604/15 |

(Continued)

OTHER PUBLICATIONS

International Search Report, PCT/US2014/057113.
Supplementary European Search Report, EP 14 84 7991, Jun. 14, 2016, pp. 7.

*Primary Examiner* — Kevin C Sirmons
*Assistant Examiner* — Amber Stiles
(74) *Attorney, Agent, or Firm* — Chapin IP Law, LLC

(57) ABSTRACT

A fluid flow manager executing on first hardware controls a flow of fluid outputted from a fluid delivery pump to a recipient. A monitor resource, executing on second hardware operating independently of the first hardware, monitors for an occurrence of a failure condition associated with the delivery of fluid. In response to detecting occurrence of a failure condition associated with delivery of the fluid, the monitor resource generates a control output. The control output can be used to perform operations such as discontinue delivery of the fluid, notify a respective caregiver of the delivery failure, etc.

14 Claims, 10 Drawing Sheets

(56) References Cited

U.S. PATENT DOCUMENTS

| | | | |
|---|---|---|---|
| 2008/0255517 A1 | 10/2008 | Nair et al. | |
| 2011/0071465 A1* | 3/2011 | Wang | A61M 1/28 604/67 |
| 2011/0257798 A1* | 10/2011 | Ali | A61M 5/16831 700/282 |
| 2012/0157920 A1 | 6/2012 | Flachbart et al. | |
| 2012/0185267 A1* | 7/2012 | Kamen | G06Q 50/22 705/2 |

* cited by examiner

MEDICAL DEVICE MANAGEMENT USING SAFETY SUPERVISOR

RELATED APPLICATIONS

This application claims the benefit of U.S. Provisional Patent Application Ser. No. 61/882,818 entitled "Integrated Infusion Device," filed on Sep. 26, 2013, the entire teachings of which are incorporated herein by this reference.

BACKGROUND

Conventional infusion pumps enable a caregiver to intravenously deliver fluid to a patient. A process of delivering fluid-based drugs using a conventional infusion pump typically requires multiple operations.

For example, a physician must first generate a medication order (prescription) specifying one or more fluid-based drugs for delivery to a particular patient in a hospital. A pharmacy in the hospital receives the medication order supplied by the physician. In accordance with the medication order, the pharmacy dispenses a corresponding physical order by providing the drugs to a caregiver for delivery to a respective patient.

In certain instances, the medication order includes multiple fluid-based drugs that need to be administered intravenously to the respective patient. In such an instance, and assuming that each of the fluid-based drugs must be delivered by a separate fluid delivery system (fluid pump), the caregiver overseeing the patient must locate multiple fluid delivery systems (fluid pumps) in the hospital. Locating one or more fluid delivery systems itself may be a difficult task because the hospital may not keep good track of unused medical equipment.

Subsequent to locating one or more needed fluid delivery systems, the caregiver typically must transport the fluid delivery systems to a site where the patient resides. At the patient's bedside, in accordance with the medication order information, the caregiver operates the one or more fluid delivery systems to intravenously deliver the corresponding prescribed fluid-based drugs to the patient. In accordance with the medical order, each fluid pump then must be individually programmed by the caregiver to intravenously dispense the fluid to the patient.

BRIEF DESCRIPTION OF EMBODIMENTS

Conventional techniques of intravenously delivering fluid to a patient suffer from deficiencies. For example, as previously discussed, operations of managing delivery of one or more fluids to a patient are tedious and can result in fluid delivery errors. Failure to properly deliver the prescribed fluid-based drugs to a corresponding patient may be harmful, or possibly fatal.

In contrast to conventional techniques, embodiments herein include unique ways of managing fluid delivery systems and related data, facilitating delivery of fluid to a recipient. More specifically, it is noted that the utility of a respective infusion pump increases significantly when the infusion pump has the ability to communicate with other devices and systems (such as a remote server) within a healthcare enterprise. For example, users such as clinicians, pharmacists, biomedical engineers, etc., interacting with the infusion pump can benefit from a robust bi-directional flow of data and services to/from the infusion pump.

The ability of an infusion pump to communicate with a remote information system over a network makes it possible for the infusion pump to perform certain tasks not possible in the past using conventional fluid pumps. For example, if an infusion device is associated with a patient, the fluid pump can communicate over the network to retrieve information about other medical devices also associated with the patient to provide appropriate treatment.

Additionally, the fluid pump can be configured to communicate with a remote server in a network to identify configuration settings associated with delivering fluid to a corresponding patient. In accordance with configuration settings, the fluid pump delivers appropriate fluid to a corresponding patient.

While the benefits of increased integration of a respective fluid pump with related information systems is clear, such increased integration exposes the fluid pump to new kinds of failures and possibly even malicious attacks. To operate a respective pump in a safe and secure manner, certain embodiments herein include isolating and/or protecting a real-time fluid flow control system from any interactions with external system components.

More specifically, one embodiment herein includes novel partitioning and segregation of hardware and/or software in a fluid delivery system to perform different useful tasks. For example, in one embodiment, a first partitioning of hardware and/or software in the fluid delivery system executes a fluid flow control algorithm to control a flow of fluid outputted from a fluid delivery pump to a recipient. A second partitioning of hardware and/or software in the fluid delivery system is segregated from the first partitioning and operates independently of the first partitioning. In one embodiment, the second partitioning executes a safety monitor algorithm. Via the safety monitor algorithm, the second partitioning monitors the first partitioning (fluid flow controller) to detect occurrence of a failure condition. Upon detection of the failure condition, the second partitioning performs one or more corrective actions/responses such as producing a control output to indicate the detected occurrence of the failure condition.

Further embodiments herein include an additional partitioning. For example, in one embodiment, the fluid delivery system as described herein can include a third partitioning of hardware and/or software (such as a communication/information manager). In one embodiment, the fluid delivery system includes a display screen communicatively coupled to the third partitioning (communication/information manager). The third partitioning can be configured to perform functions such as i) initiate display of configuration information associated with the fluid delivery pump on the display screen for viewing by a caregiver operating the fluid delivery pump, ii) receive input indicating control settings in which to control the fluid outputted from the fluid delivery pump to the recipient, etc.

As a further example embodiment, subsequent to receiving control input, the third partitioning communicates the control settings (such as a specified rate at which to deliver the fluid to the recipient) to both the first partitioning (fluid flow controller) and the second partitioning (safety monitor resource). In such an instance, as previously discussed, independent of the second partitioning and third partitioning, the first partitioning executes a first set of software instructions to control the flow of fluid to a respective recipient. The second partitioning (safety monitor resource) executes a second set of software instructions to monitor the first partitioning (fluid flow controller) and delivery of the fluid by the fluid delivery pump to the recipient.

In accordance with further embodiments, while the first partitioning controls the fluid delivery pump and a corresponding rate of delivering the fluid to the recipient, the first partitioning produces delivery information such as data indicating an estimation of the volume of the fluid outputted from a corresponding controlled fluid delivery pump to the recipient. The first partitioning forwards the delivery information to the second partitioning. The second partitioning processes the delivery information received from the first partitioning and compares it to acceptable delivery rate information. In one embodiment, in furtherance of providing safe and secure delivery of fluid to a patient, the second partitioning produces control output such as terminating the delivery of fluid, activating an alarm, etc., in response to detecting that the estimated volume of the fluid is reported by the fluid flow manager falls outside of one or more limits as indicated by acceptable delivery rate information.

Note that the control output generated by the second partitioning (safety monitor resource) can be used in any suitable manner. For example, the fluid delivery system as discussed herein can include any suitable type of notification interface such as a display screen, speaker, optical signal generator, etc. In one embodiment, in response to detecting a failure associated with delivery of fluid, the first partitioning produces an appropriate control output to control the notification interface to notify a respective entity (such as a caregiver or other suitable entity) of the occurrence of the failure condition. The notified entity can then take appropriate measures to provide corrective action associated with the failing one or more fluid delivery pumps.

As further discussed herein, note that the fluid delivery system can be operated in any of multiple different modes. For example, in one mode, the fluid delivery system (including one or more fluid delivery pumps) can be operated independently of being connected to a respective network. In such an instance, while disconnected from a respective network, the fluid delivery system operates in an autonomous manner to deliver a specified amount of fluid to a corresponding recipient.

In accordance with an alternative mode, delivery system also can be operated while communicatively coupled to a corresponding network. In this latter instance, the fluid delivery system is able to perform functions such as: receive information from a remote location over the network regarding delivery of a respective fluid to a patient, provide feedback to one or more remote locations regarding delivery fluid, etc.

As further discussed herein, the fluid delivery system can include one or more additional novel safeguards and security features to facilitate fluid delivery in any of the different operational modes.

These and other more specific embodiments are disclosed in more detail below.

Note that any of the resources as discussed herein can include one or more computerized devices, fluid delivery systems, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes computer readable storage media and/or system having instructions stored thereon. The instructions, when executed by computer processor hardware (such as first computer processor hardware, second computer processor hardware, etc.), cause the computer processor hardware to: via first hardware executing a fluid flow control algorithm, control a flow of fluid outputted from a fluid delivery pump to a recipient; via second hardware executing a monitor algorithm independently of the first hardware, monitor the first hardware to detect occurrence of a failure condition; and via the second hardware, produce a control output to indicate the detected occurrence of the failure condition The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for managing and providing safe operation of a respective fluid delivery system. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

Figure 1:
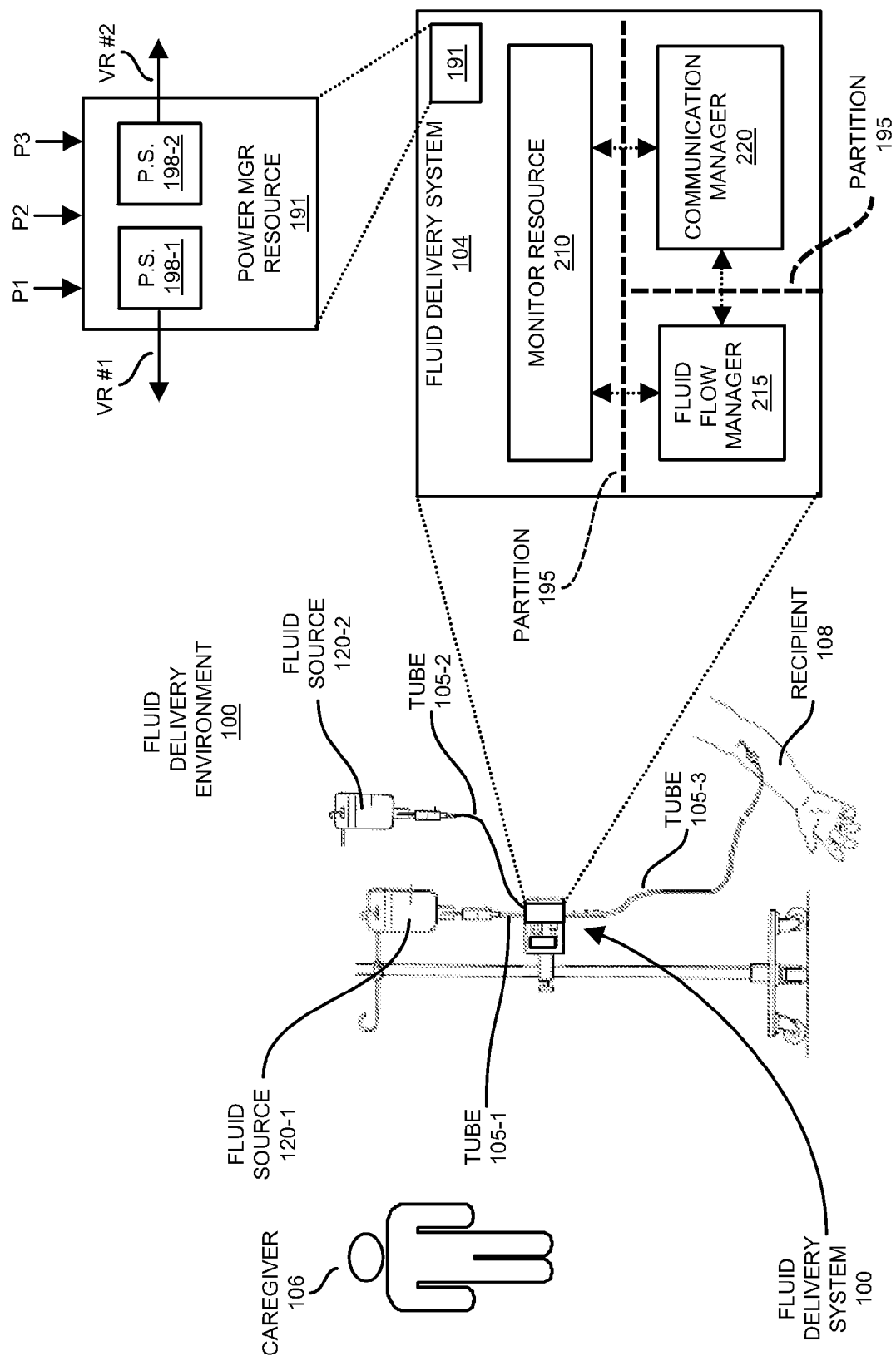
FIG. 1 is an example diagram illustrating a fluid delivery system and corresponding partitioning according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

Embodiments herein include an infusion device (fluid delivery system) that can operate independently or as part of a larger information system. In accordance with one embodiment, the infusion device has at least three operating domains, separating the measurement and control of fluid flow from the management of information, and from safety monitoring of the system. These domains can operate on separate hardware processors and communicate over a common communication bus (or alternatively support independent communication links) interconnecting the domains. As further discussed herein, the domains can be partitioned in a way that enables them to collaborate with each other, but prevents them from impeding each other and their respective operations.

As part of an information system, the fluid delivery system according to embodiments herein is capable of: sharing their data and state, retrieving information shared by other medical devices, retrieving information available from systems within the healthcare enterprise, operating using a common set of configured parameters defined for all infusion devices comprising the same information system, etc.

In one embodiment, the fluid delivery system (such as an infusion device) continues to operate (deliver fluid to a respective recipient) when disconnected (such as when severed from a network) from the larger information system.

By physically and logically isolating the operating domains, embodiments herein include implementing system wide safety and security measures such that no one failure or breach of security can disable or disrupt infusion delivery. Accordance with further embodiments, the domains can be configured to cross-check and verify each other. If an anomaly is detected, the fluid delivery system can safely halt delivery and alert appropriate personnel.

Now, more specifically, FIG. 1 is an example diagram illustrating a fluid delivery system according to embodiments herein.

As shown, fluid delivery environment 100 includes fluid source 120-1 (such as a source of a first fluid), fluid source 120-2 (such as a source of a second fluid), and so on. In general, during operation, fluid delivery system 104 controls a delivery of the fluid from the fluid source 120-1 and fluid source 120-2 to recipient 108 (any suitable type of entity such as a human, mechanical system, etc).

Fluid delivery system 104 has the ability to deliver fluid from each of the fluid sources 120 at any suitable rate. For example, the fluid delivery system 104 can be configured to deliver fluid received from fluid source 120-1 through tube 105-1 to recipient 108 (and through tube 105-3) in accordance with a first fluid delivery rate; fluid delivery system 104 can be configured to deliver fluid received from fluid source 120-2 through tube 105-2 to recipient 108 (and through tube 105-3) in accordance with a second fluid delivery rate; and so on.

As further shown, in contrast to conventional techniques, fluid delivery system 104 can be partitioned in any suitable manner to control delivery of corresponding fluid to the recipient 108. In this example embodiment, fluid delivery system 104 includes partition 195, segregating different functions and/or hardware such as monitor resource 210, fluid flow manager 215, communication manager 220, etc.

Each of the different resources (such as monitor resource 210, fluid flow manager 215, and communication manager 220) residing in fluid delivery system 104 can be powered by different sets of one or more voltage rails. For example, as shown, the fluid delivery system 104 can include power manager resource 191. In this example embodiment, power manager resource 191 includes first power supply 198-1 and second power supply 198-2.

During operation, power manager resource 191 receives power input (P1, P 2, P3, . . .) from multiple sources including a first source (such as 120 volts AC from a wall socket), a second source (such as a first battery), a third source (such as a second battery), and so on. By way of non-limiting example embodiment, the first source acts as primary power. The second source is a backup resource in case the primary power source fails. The third source is a backup resource in case the second power source fails.

In one embodiment, each of the power supplies 198 receives input power from each of multiple sources. For example, in one embodiment, power supply 198-1 receives power input P1 from a first power source; power supply 198-1 receives power input P2 from a second power source; power supply 198-1 receives power input P3 from a third power source.

Based on power input P1, power input P2, and/or power input P3, power supply 198-1 produces one or more voltages VR#1 to power circuitry such as fluid flow manager 215 and communication manager 220. As previously discussed, any of the different received power inputs can be backup power with respect to each other. Thus, even if one or more power inputs P1, P2, or P3 happens to fail, the power supply 198-1 is able to use at least one healthy power input to produce a set of one or more output voltages VR#1 to power circuitry such as fluid flow manager 215 and communication manager 220.

Additionally, power supply 198-2 receives power input P1 from the first power source; power supply 198-2 receives power input P2 from the second power source; power supply 198-2 receives power input P3 from the third power source. Based on power input P1 power input P2, and/or power input P3, power supply 198-2 produces one or more voltages VR#2 to power circuitry such as monitor resource 210. As previously discussed, any of the power inputs can be backup power with respect to each other. Thus, even if one or more power inputs P1, P2, or P3 happens to fail, the power supply 198-1 is able to use at least one healthy power input to produce a set of one or more output voltages VR#2 to power circuitry such as monitor resource 210. As further discussed below, partitioning of the fluid delivery system 104 to provide different functionality in accordance with partition 195 (to produce independently operating circuitry) allows safer and more secure delivery of one or more fluids to a respective recipient 108.

Figure 2:
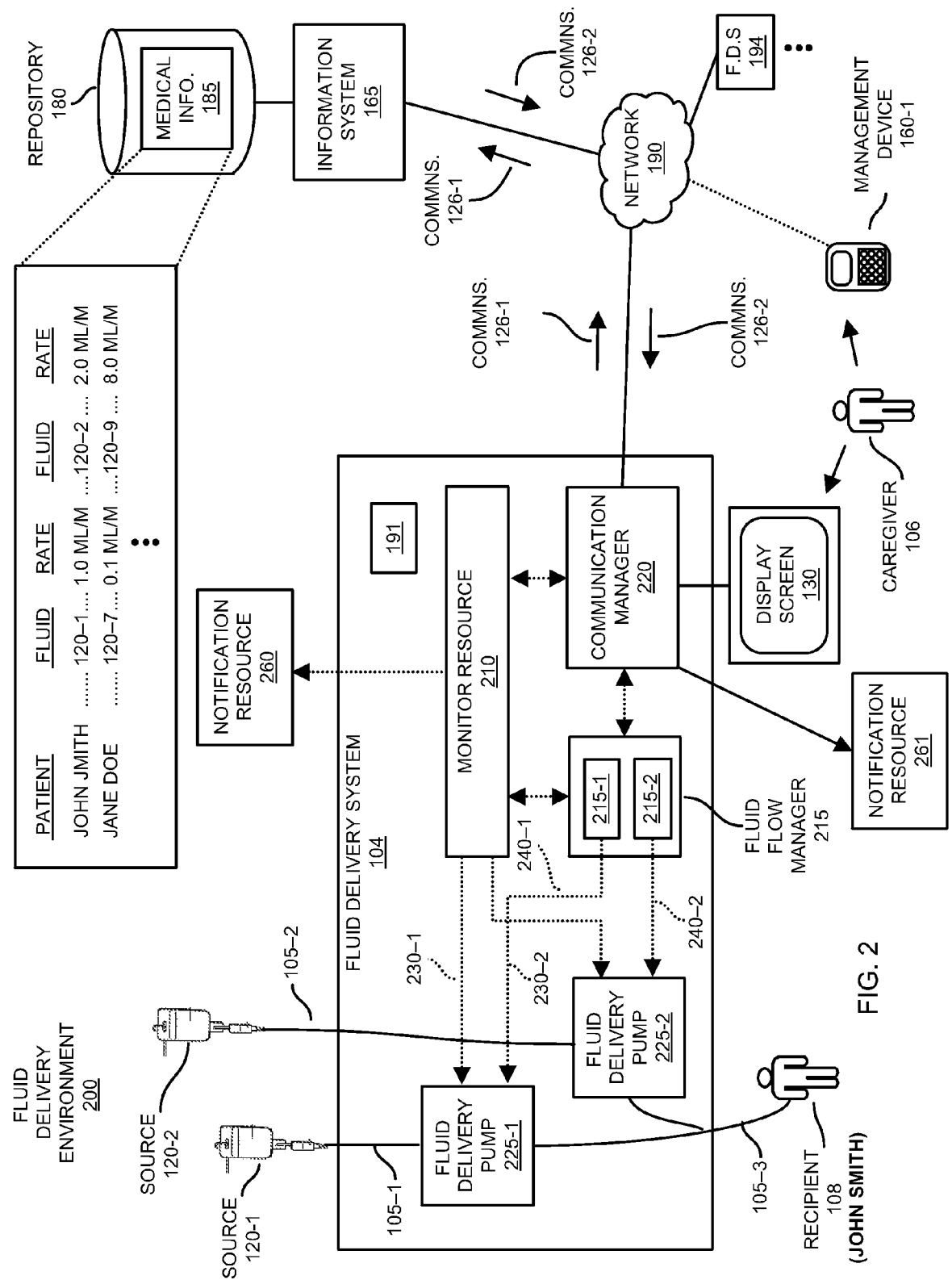
FIG. 2 is an example diagram illustrating functionality associated with a fluid delivery system according to embodiments herein.

FIG. 2 is an example diagram illustrating operational use of a respective fluid delivery system according to embodiments herein.

As previously discussed, one embodiment herein includes novel partitioning and segregation of hardware in a fluid delivery system 104 to perform different useful tasks.

For example, in one embodiment, fluid delivery system 104 includes: fluid flow manager 215 (a first partitioning of hardware and/or software), monitor resource 210 (a second partitioning hardware and/or software), and communication manager 220 (a third partitioning of hardware and/or software).

By way of non-limiting example embodiment, the communication manager 220 and fluid flow manager 215 each can operate on a corresponding dedicated core of a multi-core processor hardware. That is, the communication manager 220 can be configured to execute on a first core of the multi-core processor hardware; the fluid flow manager 215 can be configured to execute on a second core of the multi-core processor hardware; and so on. The monitor resource 210 operates on separate processor hardware independent of the multi-core processor hardware.

Alternatively, each of the processes including monitor resource 210, communication manager 220, and fluid flow manager 215 each can execute on their own processor hardware. A first communication link (communication interface) in the fluid delivery system 104 supports communications between the monitor resource 210 and communication manager 220; a second communication link (communication interface) in fluid delivery system 104 supports communications between the communication manager 220 and the fluid flow manager 215; a third communication link (communication interface) in fluid delivery system 104 supports communications between the fluid flow manager 215 and the monitor resource 210. Each of the first communication link, second communication link, and the third communication link can operate independently of each other such that a failure of a single communication link does not disable the whole system.

If desired, the monitor resource 210 can be further isolated from the operational domains associated with fluid flow manager 215 and communication manager 220. For example, as previously discussed, the fluid flow manager 215 and the communication manager 220 can be powered by a first set of one or more voltage rails VR#1 as produced by a first power supply 198-1 in power manager resource 191; the monitor resource 210 and corresponding hardware can be powered by a second set of one or more voltage rails VR#2 as produced by power supply 198-2 in power manager resource 191.

The monitor resource 210 can include persistent storage (such as memory) to store status and error codes.

As further shown, communication manager 220 is communicatively coupled to one or more resources. For example, in one embodiment, the fluid delivery system 104 includes display screen 130. Via display screen 130, the caregiver 106 is able to control operations associated with the fluid delivery system 104 in view delivery information. For example, in one embodiment, the display screen 130 displays a corresponding graphical user interface access information, allowing the respective caregiver 106 to view information associated with delivering fluid and input control information to control delivering fluid in a desired manner.

In one embodiment, input from the caregiver 106 (or other suitable resource) controls the programming and/or operation of the fluid delivery pumps 225. The graphical user interface displayed on display screen 130 optionally includes a web browser or other suitable resource capable of navigating to both internal content (such as content stored locally in the fluid delivery system 104) and external content (such as content stored remotely in repository 180 or other storage resources).

In one embodiment, the communication manager 220 is separated into two domains, each running within its own software process. The first domain of communication manager 220 can be configured to continue to manage the user experience (such as caregiver 106 experience) as well as manage all outbound communications over network 190 to information system 165 (or the resources in network 190). Further in this example, the second domain associated the communication manager 220 (a.k.a., the data domain) can be configured to manage the importing and validation of data from all external sources in network 190. This includes, but may not be limited to, the browsing of information on a remote server (such as information system 165) using technologies such as, but not limited to, a web browser.

The data domain of communication manager 220, though potentially susceptible to malicious attacks over network 190, isolates (such as via a firewall) the other domains (such as monitor resource 210, fluid flow manager 215, etc.) from those attacks.

Note that in one embodiment, in the event that the fluid delivery system 104 disconnects from network 190, the fluid delivery system 104 can be configured to persist any data it intends to share with the remote servers (such as information system 165) in its own local storage (i.e., a repository located within fluid delivery system 104). Subsequent to revival of a respective connection (such as a wired or wireless communication link) between the communication manager 220 and the network 190, the fluid delivery system (and more specifically communication manager 220) forwards the stored fluid delivery information to a respective server resource such as information system 165.

In accordance with yet further embodiments, data sourced by one fluid delivery system 104 (an infusion device) can be made available to other fluid delivery systems (such as a second fluid delivery system 194, etc.) associated with the information system 165. Examples of shared data include infusion information, alarm information, device status information, etc. Thus, fluid delivery system 194 can be notified of the status of fluid delivery by fluid delivery system 104.

In one embodiment, the exchange of information between fluid delivery systems is managed by information system 165. An infusion device (a.k.a., fluid delivery system 104) can request this information and then present it to the user or use it to advise the user during the programming and/or administration of an infusion on that device.

When a network connection over network 190 is not available, the fluid delivery system 100 can be configured to continue to operate as an infusion device without the advanced features made possible through system connectivity.

Further in this example embodiment, the Information Domain (communication manager 220) interacts with the larger information system, passing information to that system and retrieving information from it on an as needed basis. It also can be configured to control the user (such as caregiver 106) experience, presenting information to the user and providing the means for the user to interact with the fluid delivery system 104. By further way of non-limiting example embodiment, the information domain is the only domain in the infusion device that interacts with external components, and it is therefore responsible for isolating the other domains from any security breaches. If such a breach occurs, it is handled and contained by the information domain (communication manager 220) without causing the fluid delivery pump 225 to operate in an unsafe manner.

As further discussed below, in one embodiment, the monitor resource 210 (Safety Domain) monitors the other two operational domains (such as communication manager 220 and fluid flow manager 215) for proper and safe operation. The safety domain can be configured to monitor both the fluid flow and information domain, ensuring that both are operational at appropriate times. In the event that either fails, the safety domain (monitor resource 210) can be configured to place the pump into a safe state, which may include a notification or shutdown of the flow of fluids by fluid delivery pumps 225.

The fluid delivery system 104 can be viewed as a component of an overall Infusion Management System (such as information system 165). The fluid delivery system 104 interacts with services available through the Infusion Management System. Through these services, the fluid delivery system 104 may share its data and state information, retrieve information shared by other medical devices, retrieve information gathered from other systems in the hospital enterprise and retrieve system wide parameters configured to define the operation of the infusion devices, etc.

In yet a further non-limiting example, the information system 165 exposes the fluid delivery system 104 to one or more (information) services. These services may utilize one or more communication mechanisms. For example, one service may be capable of communicating using RESTful web services while another, performing the same function, may support SOAP based web services. Each service is capable of supporting one or more functions, including but not limited to, accepting infusion data, returning patients in a specified clinical unit, orders for a specified patient or details of all infusions being delivered for a specified patient.

During operation, as previously discussed, the communication manager 220 facilitates conveyance of communications. Initially, assume that the caregiver 106 operates the fluid delivery system 104 to associate the respective fluid delivery system 104 to a corresponding recipient 108. Based on input from the caregiver 106, the communication manager 220 communicates with information system 165 to associate the fluid delivery system 104 to the recipient 108 (John Smith).

Upon receipt, the server (information system 165) not only registers the new association between the respective fluid delivery system 104 and the recipient 108, it also keeps track of any previous associations between other fluid delivery systems and the recipient 108. Accordingly, since information system 165 keeps track of associations, to learn of current associations between the recipient 108 and any of one or more fluid delivery systems in fluid delivery environment 200, the caregiver 106 can access medical information stored by information system 165.

Once the information system 165 associates the fluid delivery system 104 with the a respective patient, the fluid delivery system 104 is able to request information about other matters associated with the respective patient, including details about ongoing infusions.

In this example, assume that the caregiver 106 wishes to use the fluid delivery system 104 to deliver one or more fluids to respective recipient 108. In such an instance, the caregiver 106 inputs information such as the name of the recipient 108 (John Smith) through display screen 130 or other suitable resource to associate the fluid delivery system 104 with recipient 108. The caregiver 106 also may input information indicating his/her identity such that information system 165 is aware of the identity of the caregiver 106 administering care (such as delivery of fluids) to the recipient 108.

In one embodiment, based on the received input in communications 126-1 from communication manager 220, the information system 165 creates an association between the fluid delivery system 104, the recipient 108, and the caregiver 106. The associations may then be used to support the delivery process. For example, because the recipient 108 is associated with the caregiver 106, the communication manager 220 and/or information system 165 is then able to transmit notification information such as messages to the caregiver 106 (for display on either or both of display screen 130 and/or management device 160-1 operated by the respective caregiver 106) in the event of an emergency associated with recipient 108 or fluid delivery system 104.

Fluid delivery system 104 can be programmed to deliver fluid in any suitable manner. In one embodiment, the downloading and execution of fluid delivery configuration settings from information system 165 can be handled automatically by the fluid delivery system 104. In certain instances, the installation of fluid delivery configuration information can be handled while the fluid delivery system 104 is currently delivering fluid to a recipient 108. If the fluid delivery system 104 loses connectivity with network 190, previously downloaded configuration information can still be available locally to deliver respective fluid to the recipient 108 because the fluid delivery system 104 can operate independently of being connected to network 190 as previously discussed.

Assume further in this example that the caregiver 106 inputs a query through the display screen 130 to learn if any fluids are to be administered to the recipient 108 associated with fluid delivery system 104. Via communications 126-1, the communication manager 220 communicates the query over network 190 to information system 165. In this instance, the information system 165 maps the name of the recipient 108 (associated with fluid delivery system 104) to corresponding medical information 185 associated with recipient 108 stored in repository 180.

By way of non-limiting example embodiment, the medical information 185 (such as a medical order prescribed by a doctor) can indicate configuration settings associated with delivery of one or more fluids to be administered to the recipient 108. For example, as shown, the medical information 185 associated with the recipient 108 can indicate to deliver a first type of fluid at a first delivery rate to recipient 108; the medical information 185 can indicate to deliver a second type of fluid at a second delivery rate to recipient 108; and so on.

Via further 126-2, information system 165 transmits fluid delivery configuration settings such as medical information 185 associated John Smith over network 190 (such as a packet-switched network) to the communication manager 220. In one embodiment, the fluid delivery system 104 uses the configuration settings indicated by the information system 165 to perform one or more specific such as deliver the respective fluids to the recipient 108.

Note that the fluid delivery configuration settings as indicated by medical information 185 may be created with tools executed on the information system 165 and then published so that the medical information 185 is available to all infusion devices available in the fluid delivery environment 200. Once published (i.e., made available from information system 165), any fluid delivery systems in environment 200 have access to that information and can download and install configuration settings to administer fluid to the appropriate patient.

Further in this example, in response to receiving the medical information 185 associated with John Smith from information system 165, the communication manager 220 initiates display of the medical information 185 (associated John Smith) on display screen 130. Via the display medical information (such as derived from medical information 185) on display screen 130, the caregiver 106 is notified of information such as the type of fluid to be delivered to the recipient 108, the rate at which the fluids are to be delivered, etc.

The display of medical information 185 associated John Smith on display screen 130 for viewing by caregiver 106 reduces the likelihood of making errors associated with delivery of one or more different fluids to a corresponding patient. In this example embodiment, the caregiver 106 is able to retrieve the medical information 185 from a trusted source (that is, information system 165 and respective repository 180), verify the medical information 185, and then proceed with proper delivery of fluid to a respective patient.

In accordance with the displayed medical information associated with John Smith, if he/she has not already done so, the caregiver 106 physically retrieves fluid source 120-1 (first specified type of fluid) and fluid source 120-2 (second specified type of fluid) from an entity such as an apothecary, pharmacist, etc.

Caregiver 106 then connects fluid source 120-1 to fluid delivery pump 225-1 via tube 105-1; caregiver 106 connects fluid source 120-2 to fluid delivery pump 225-2 via tube 105-2. The caregiver 106 couples tube 105-3 to input respective fluid into recipient 108.

To dispense fluid from the fluid source 120-1 and/or fluid source 120-2, the caregiver 106 provides further input (such as one or more commands) to communication manager 220 such as through display screen 130, remote management device 160-1, a corresponding keyboard or touchscreen associated with the fluid delivery system 104.

Communication manager 220 receives the one or more control commands from the caregiver 106 (or other resources such as information system 165) and communicates the one or more control commands to fluid flow manager 215. Additionally, note that communication manager 220 can be configured to forward the control information associated with delivery of fluids to monitor resource 210.

Accordingly, the communication manager 220 apprises both the fluid flow manager 215 and the monitor resource 210 of the delivery operations that are to be performed by each of the one or more fluid delivery pumps 225.

As its name suggests, in accordance with the configuration settings (such as fluid flow delivery rates) as indicated by the communication manager 220, the fluid flow manager 215 controls a flow of fluid through one or more sources 120 to recipient 108. In one embodiment, fluid flow manager 215 executes one or more fluid flow control algorithms (on corresponding dedicated hardware in fluid delivery system 104) to control a flow of fluid outputted from each of one or more fluid delivery pumps 225 to recipient 108.

By further way of example, in one embodiment, fluid flow manager 215 includes fluid flow manager 215-1 and fluid flow manager 215-2—one controller for each respective fluid delivery pump.

During operation, fluid flow manager 215-1 generates one or more control signals 230-2 to control fluid delivery pump 225-1 in accordance with control input (such as in a manner specified by medical information 185 associated John Smith) received from communication manager 220; fluid flow manager 215-2 produces one or more control signals 240-2 to control fluid delivery pump 225-2 in accordance with control input (such as in a manner specified by medical information 185 associated John Smith) received from communication manager 220; and so on.

As further shown, and as previously discussed, fluid delivery system 104 includes monitor resource 210 (such as a partitioning of hardware and/or software) segregated from and operating independently of the fluid flow manager 215. In one non-limiting example embodiment, the monitor resource 210 monitors feedback (such as from fluid flow manager 215) associated with delivery of fluid to a respective recipient 108. More specifically, the monitor resource 210 can be configured to verify that fluids continue to be delivered at the rate configured by the user, based on feedback from a suitable resource such as the fluid flow manager 215, that one or more of the fluid delivery pumps 225 (fluid delivery pump 225-1 and fluid delivery pump 225-2) are operating properly, and so on.

The feedback from the fluid flow manager 215 and/or fluid delivery pumps 225 can include any suitable type of information. For example, in one embodiment, the feedback from fluid flow manager 215 notifies the monitor resource 210 of an estimated rate at which each of one or more fluids are delivered to the corresponding recipient 108; in accordance with another embodiment, the feedback from the fluid flow manager 215 is a watchdog keep-alive or heartbeat signal generated by the fluid flow manager 215 to the monitor resource 210 to indicate that the fluid flow manager 215 is still functioning properly (such as that the fluid flow manager 215 is properly powered and executing appropriate instructions); and so on.

In accordance with further embodiments, if the communication manager 220 does not receive an appropriate watchdog keep-alive or heartbeat signal from the fluid flow manager 215 within a particular interval of time, the monitor resource 210 can be configured to display notification of this detected event as a failure condition. Additionally, the monitor resource 210 can be configured to produce appropriate control output such that the notification resource 260 produces an audible sound to indicate the occurrence of the failure condition.

Upon detection of a failure condition associated with a respective fluid delivery based on feedback (such as fluid delivery information) or lack of feedback (such as failure to receive a watchdog keep alive signal), the monitor resource 210 produces one or more control outputs to notify the respective caregiver 106 or other entity of the failure condition. In accordance with yet further embodiments, the fluid delivery system 104 includes notification resource 261 controlled by communication manager 220. Notification resource 261 can be or include any suitable resource to convey a message (visual, audio, etc., indicating occurrence of a respective failure) to a particular party or resource in fluid delivery environment 200.

As a more specific example of operation, in accordance with the input from the respective caregiver 160 and/or from the medical information 185 received from information system 165, assume that the communication manager 220 notifies the fluid flow manager 215-1 to deliver fluid from source 120-1 (a first type of fluid) at a first delivery rate such as 1.0 mL (milliliters) per minute. Assume further that the communication manager 220 notifies the fluid flow manager 215-2 to deliver fluid (a second type of fluid) from source 120-2 at a second delivery rate such as 2.0 mL per minute. This is specified by the medical information 185 associated with John Smith.

While the respective fluid flow manager 215 controls the fluid delivery pumps 225 and a corresponding rate of delivering respective fluid to the recipient 108, each of the fluid flow manager 215 produces fluid delivery information such as data indicating an estimated volume of the fluid outputted from the respective fluid delivery pump to the recipient 108. The fluid flow manager 215 forwards the delivery information to monitor resource 210 for analysis.

Figure 3:
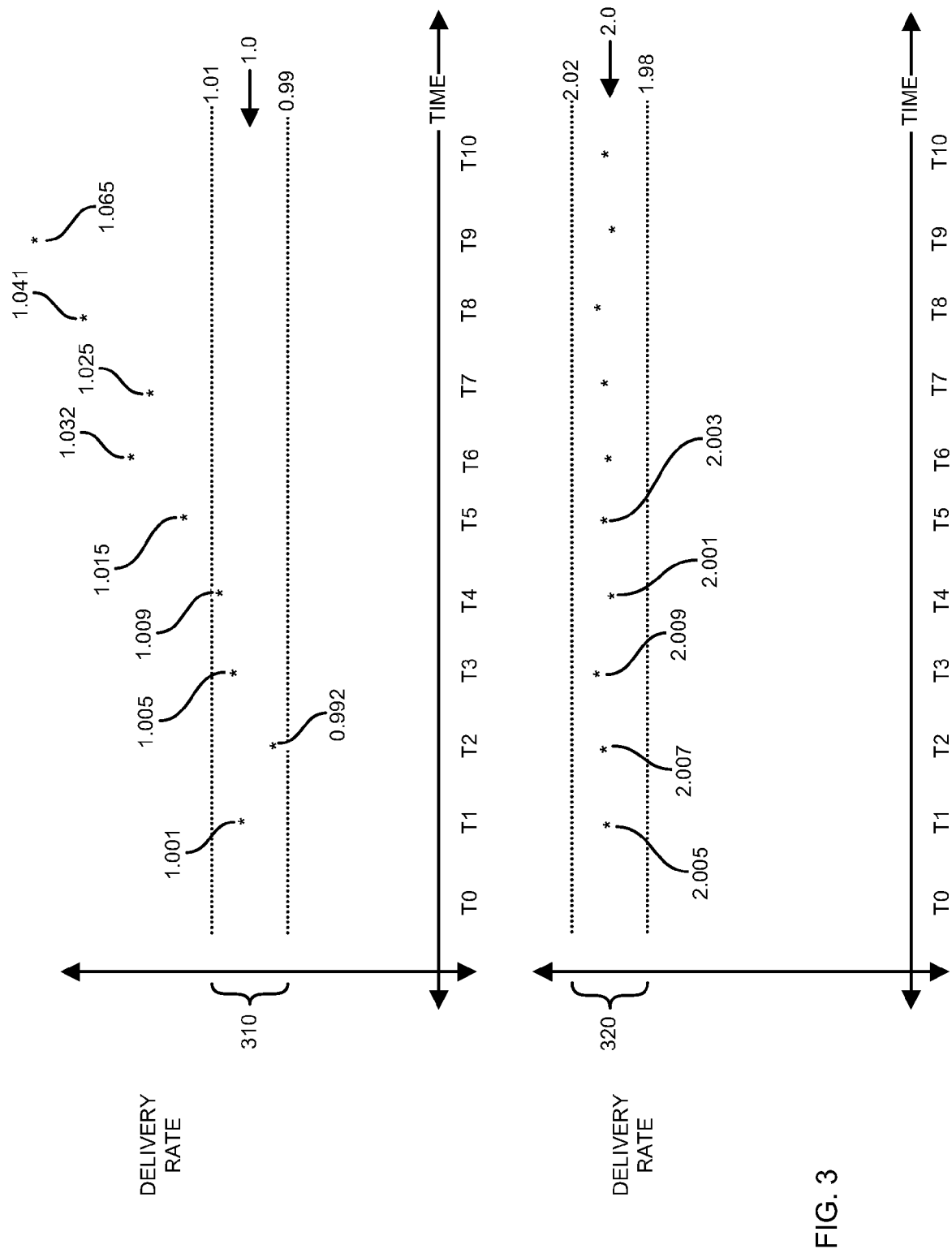
FIG. 3 is an example timing diagram illustrating an independently operating monitor resource monitoring delivery data received from multiple fluid flow managers according to embodiments herein.

The monitor resource 210 processes the delivery information received from the fluid flow manager 215 and compares such information to acceptable delivery rate information as further shown in FIG. 3.

FIG. 3 is an example timing diagram illustrating analysis and monitoring of fluid delivery according to embodiments herein.

As previously discussed, initially, an appropriate entity such as the caregiver 106 programs the fluid delivery system 104 to deliver fluid to a respective recipient 108. In response to programming, the communication manager 220 notifies the fluid flow manager 215 and the monitor resource 210 of the flow rate for delivery of one or more fluids. Once started, the fluid flow manager 215 sends the monitor resource 210 an indication of the fluid flow rate the respective one or more fluid delivery pumps 225 are delivering and the flow rate it is attempting to deliver. The monitor resource 210 expects to receive the updated delivery flow information from the fluid flow manager 215 at a fixed rate.

During operation, if the fluid flow manager 215 ceases to send updates of fluid delivery information to the monitor resource 210 at the expected update rate, the monitor resource 210 will initiate a system fault and shutdown the flow of fluids. Thus, if the monitor resource 210 fails to receive updated flow information from the fluid flow manager 215 in a timely manner, the monitor resource 210 will initiate shutting down one or more of the fluid delivery pumps 225.

Additionally, if the difference between the actual flow rate (as reported by the fluid flow manager 215 for one or more sample periods) falls outside expected limits, the monitor resource 210 (safety processor) will initiate a system fault and shutdown the flow of fluids by fluid delivery pumps 225 to the recipient 108.

As shown in FIG. 3 and previously discussed, the monitor resource 210 receives fluid delivery status information from fluid flow manager 215-1 at or around time T1 indicating an estimated amount of fluid (such as 1.001 mL per minute) from fluid source 120-1 that fluid delivery pump 225-1 delivers to recipient 108 in an interval such as between approximately time T0 and T1; the monitor resource 210 receives fluid delivery information from fluid flow manager 215-1 at or around time T2 indicating an estimated amount of fluid (such as 0.992 mL per minute) from fluid source 120-1 that fluid delivery pump 225-1 delivers to recipient 108 in an interval such as between approximately time T1 and T2; the monitor resource 210 receives fluid delivery status information from fluid flow manager 215-1 at or around time T3 indicating an estimated amount of fluid (such as 1.005 mL per minute) from fluid source 120-1 that fluid delivery pump 225-1 delivers to recipient 108 in an interval such as between approximately time T2 and T3; the monitor resource 210 receives delivery information from fluid flow manager 215-1 at or around time T4 indicating an estimated amount of fluid (such as 1.009 mL per minute) from fluid source 120-1 that fluid delivery pump 225-1 delivers to recipient 108 between approximately time T3 and T4; the monitor resource 210 receives delivery information from fluid flow manager 215-1 at or around time T5 indicating an estimated amount of fluid (such as 1.015 mL per minute) from fluid source 120-1 that fluid delivery pump 225-1 delivers to recipient 108 between approximately time T4 and T 5; and so on as shown.

As further shown, the monitor resource 210 receives fluid delivery status information from fluid flow manager 215-2 at or around time T1 indicating an estimated amount of fluid (such as 2.005 mL per minute) from fluid source 120-2 that fluid delivery pump 225-2 delivers to recipient 108 in an interval such as between approximately time T0 and T1; the monitor resource 210 receives fluid delivery status information from fluid flow manager 215-2 at or around time T2 indicating an estimated amount of fluid (such as 2.007 mL per minute) from fluid source 120-2 that fluid delivery pump 225-2 delivers to recipient 108 in an interval such as between approximately time T1 and T2; the monitor resource 210 receives fluid delivery status information from fluid flow manager 215-2 at or around time T3 indicating an estimated amount of fluid (such as 2.009 mL per minute) from fluid source 120-2 that fluid delivery pump 225-2 delivers to recipient 108 between approximately time T2 and T3; the monitor resource 210 receives fluid delivery status information from fluid flow manager 215-2 at or around time T4 indicating an estimated amount of fluid (such as 2.001 mL per minute) from fluid source 120-2 that fluid delivery pump 225-2 delivers to recipient 108 between approximately time T3 and T 4; the monitor resource 210 receives fluid delivery status information from fluid flow manager 215-2 at or around time T5 indicating an estimated amount of fluid (such as 2.003 mL per minute) from fluid source 120-2 that fluid delivery pump 225-2 delivers to recipient 108 between approximately time T4 and T5; and so on as shown.

In one embodiment, the monitor resource 210 receives information indicating acceptable delivery ranges (such as range 310, range 320, etc.) for each of the fluids. The information can be received from any suitable resource such as from information system 165, from caregiver 106, etc.

The monitor resource 210 compares the received flow delivery information to acceptable delivery ranges. For example, the monitor resource 210 verifies that the estimated fluid delivered from the fluid source 120-1 to the recipient 108 during each of one or more time samples (such as each second long-time sample, minute-long time sample, etc.) falls within an acceptable delivery rate range 310 between 0.99 and 1.01 mL per minute. The monitor resource 210 verifies that the estimated fluid delivered from the fluid source 120-2 to the recipient 108 during one or more time samples (such as each minute-long time sample) falls within an acceptable delivery rate range 320 between 1.98 and 2.02 mL per minute.

In this example, the monitor resource 210 detects that fluid delivery pump 225-1 experiences a failure condition at or around time T5 -T10 in which the fluid delivery pump 225-1 delivers an excess amount of fluid from fluid source 120-1 to recipient 108. In other words, at or around time T5, the monitor resource 210 receives feedback (estimated delivery of 1.015 mL per minute) from the fluid flow manager 215-1 indicating that the fluid delivery pump 225-1 delivers 1.015 mL per minute, which falls outside the acceptable delivery range 310 between 0.99 and 1.01 mL per minute.

In response to detecting a failure condition such as that the estimated delivery rate for one or more fluid delivery cycles falls outside of the acceptable delivery range 310, the monitor resource 210 produces control output.

Control output generated by the monitor resource can be used to perform any suitable one or more functions. For example, in one embodiment the control output from the monitor resource 210 can be configured to perform operations such as: i) terminate delivery of the fluid in fluid source 120-1 by the fluid delivery pump 225-1 to the recipient 108, ii) provide notification of the failure to a respective entity such as caregiver 106, etc.

In one embodiment, the monitor resource 210 controls notification resource 160 in FIG. 2 to generate an audible or visual indication of the failure condition.

In accordance with another embodiment, the monitor resource 210 notifies communication manager 220 of the failure. Communication manager 220, in turn, initiates display of a corresponding message on display screen 130 indicating occurrence of the failure condition. Additionally or alternatively, the communication manager 220 can be configured to generate an audible alarm to provide notification of the failure condition.

In accordance with another embodiment, the monitor resource 210 notifies communication manager 220 of the failure condition. The communication manager 220 initiates one or more communications over network 190 to any of one or more resources such as information system 165, management device 160-1 operated by caregiver 106, etc.

The notified one or more entities (such as caregiver 106, one or more doctors, administrators of information system 165, etc.) receiving the failure notification then take appropriate measures to provide corrective action associated with the failing fluid delivery pump.

Note that the fluid delivery system 104 as discussed herein can be operated in any of multiple different modes as previously discussed. For example, in one mode, the fluid delivery system can be operated independently of being connected to a respective network 190. In such an instance, the fluid delivery system operates in an autonomous manner to deliver (or continue to deliver) a specified amount of fluid to a corresponding recipient 108 even though transmissions of communications over network 190 happen to fail.

In accordance with an alternative mode, the fluid delivery system 104 can be configured to operate while communicatively coupled to corresponding network 190. In this latter instance, the fluid delivery system 104 is able to perform functions such as: receive information from a remote location (such as from information system 165) over the network 190 regarding delivery of a respective fluid to a patient, provide feedback from the fluid delivery system 104 to the information system 165. The fluid delivery system 104 can include novel safeguards and security features to facilitate safe fluid delivery in while any of the different modes.

Figure 4:
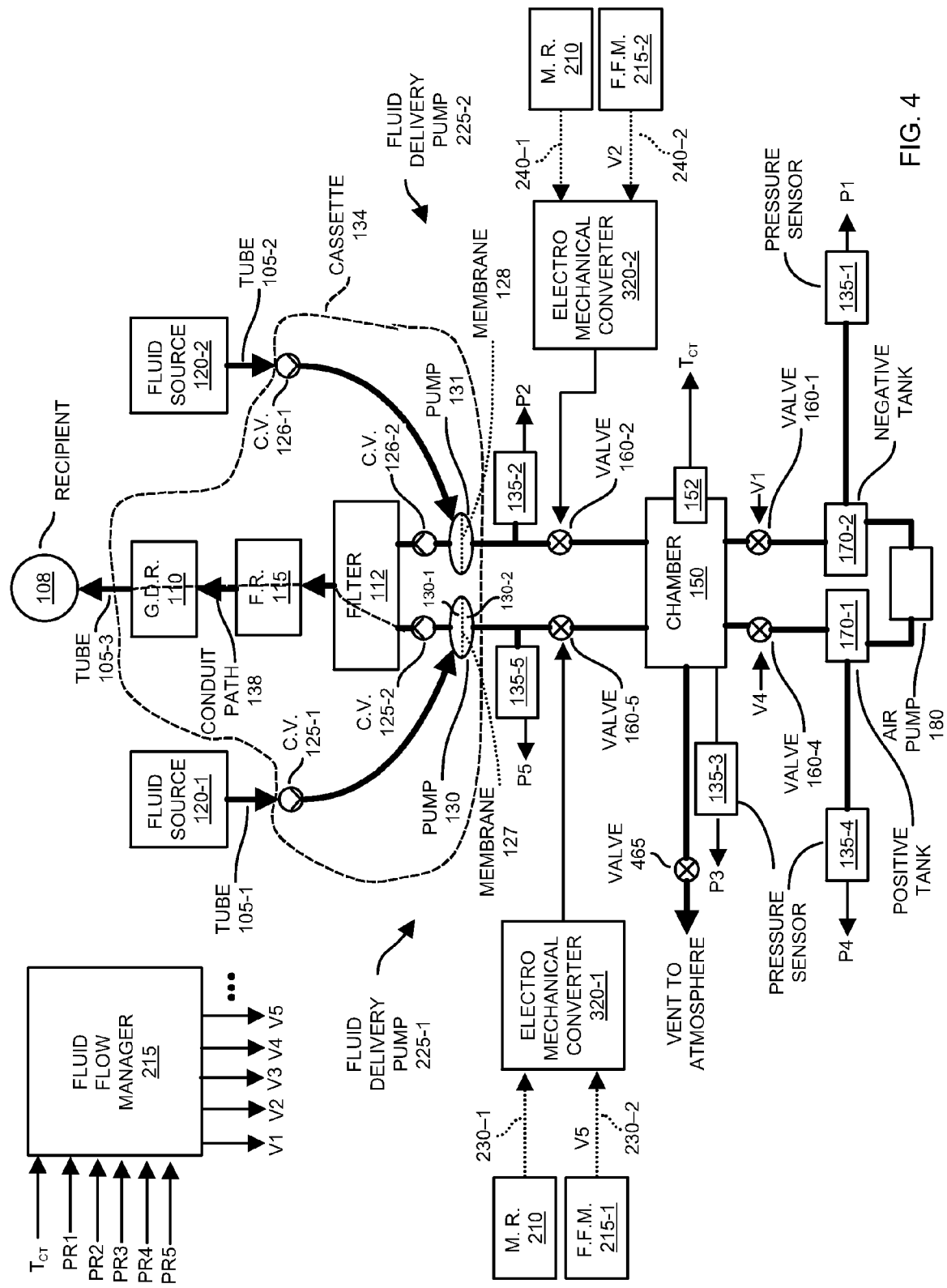
FIG. 4 is an example diagram illustrating a detailed operation of a fluid delivery pump according to embodiments herein.

FIG. 4 is an example diagram illustrating functional components and operation of respective fluid delivery pumps according to embodiments herein.

As shown, each of the fluid delivery pumps 225 includes appropriate components to facilitate delivery of fluid to a respective recipient 108.

For example, in one embodiment, fluid delivery pump 225-1 includes check valve 125-1, check valve 125-2, diaphragm pump 130, pressure sensor 135-5, and valve 160-5. Fluid delivery pump 225-2 includes check valve 126-1, check valve 126-2, diaphragm pump 131, pressure sensor 135-2, and valve 160-2.

Certain components in FIG. 4 are common to both the fluid delivery pumps 225. For example, common components include: gas detection resource 110, flow resistor 115, filter 112, chamber 150, pressure sensor 135-3, temperature sensor 152, valve 160-4, valve 160-1, pressure sensor 135-4, positive tank 170-1, negative tank 170-2, and air pump 180.

The fluid flow manager 215 of the fluid delivery system 104 controls operation of diaphragm pumps 130 and 131 in disposable cassette 134 to precisely deliver fluid from one or more fluid sources such as fluid source 120-1 and fluid source 120-2 to a respective recipient 108.

In one embodiment, the flow of liquid through the system 104 is controlled by adjustments to the drive pressure from the positive tank 170-1 and a variable hydraulic resistor (component such as fluid resistor 115) that is controlled by a motor or other suitable resource. Flow rate is measured using periodic volume calculations described below, and the control parameters are adjusted accordingly to drive the error between measured flow rate and target flow rate to zero.

Pump Cycle Overview

In accordance with yet further embodiments, a pump cycle associated with a respective diaphragm pump is defined as a motion of drawing fluid into a diaphragm pump and then applying pressure to the diaphragm pump to deliver the fluid to a recipient. In accordance with a specific non-limiting example embodiment, a pump cycle can be defined as at least partially moving of the membrane 127 in the diaphragm pump 130 from one extreme (such as "full") to another extreme (such as "empty").

As shown in FIG. 4, membrane 127 divides the diaphragm pump 130 to include chamber 130-1 and chamber 130-2. Membrane 127 prevents fluid in chamber 130-1 from passing to chamber 130-2, and vice versa.

The membrane 127 dividing diaphragm pump 130 into chamber 130-1 and chamber 130-2 is flexible. When a negative pressure is applied to chamber 130-2, the volume of chamber 130-1 expands and draws fluid from fluid source 120-1 into chamber 130-1.

Conversely, when a positive pressure is applied to chamber 130-2, the volume of chamber 130-1 decreases, expelling fluid from chamber 130-1 downstream through conduit path 138 to a respective recipient 108.

In one embodiment, the total volume or capacity of chamber 130-1 and chamber 130-2 is substantially constant regardless of the position of the membrane 127. Based on knowing the volume of fluid in chamber 130-2, one is able to determine a corresponding volume of chamber 130-1. For example, if the total volume of the diaphragm pump 130 is Vtotal, and the volume of chamber 130-2 is V2, the fluid delivery system 100 can determine the volume of chamber 130-1 by subtracting V2 from Vtotal.

Diaphragm pump 131 associated with fluid delivery pump 225-2 operates in a similar manner as diaphragm pump 130. Membrane 128 divides the diaphragm pump 131 to include chamber 131-1 and chamber 131-2. Membrane 128 prevents fluid in chamber 131-1 from passing to chamber 131-2, and vice versa.

The membrane 128 dividing diaphragm pump 131 into chamber 131-1 and chamber 131-2 is flexible. When a negative pressure is applied to chamber 131-2, the chamber 131-1 draws fluid from fluid source 120-2 into chamber 131-1. Conversely, when a positive pressure is applied to chamber 131-2, the diaphragm pump 131 expels fluid from chamber 131-1 downstream to a respective recipient 108.

In a similar manner as previously discussed for diaphragm pump 130, the total volume or capacity of chamber 131-1 and chamber 131-2 is substantially constant regardless of the position of the membrane 128. Based on knowing the volume of fluid in chamber 131-2, the fluid flow manager 215 is able to determine a corresponding volume of chamber 131-1. For example, if the total volume of the diaphragm pump 131 is Vtotal, and the volume of chamber 131-2 is determined as being V2, the fluid delivery system 100 can determine the volume of chamber 131-1 by subtracting V2 from Vtotal.

In this example embodiment, as shown in FIG. 4, temperature sensor 152 measures a temperature (e.g., TTC) of gas in chamber 150 (common tank) and provides a baseline from which to estimate the temperatures of gases in one or more of the following resources: chamber 150, pump chamber 130-2, positive tank 170-1, negative tank 170-2, etc.

As further discussed below, estimation of the temperature enables a more accurate assessment of how much of fluid in pump chamber 130-1 has been pumped in a direction towards the target recipient 108 over conduit path 138 (such as a path from diaphragm pump 130 through a combination of check valve 125-2, filter 112, fluid resistor 115, gas detection resource 210, and tube 105-3 to recipient 108).

Initially, to fill the chamber 130-1 with fluid from fluid source 120-1, the fluid flow manager 215 of fluid delivery system 100 applies a negative pressure or vacuum to chamber 130-2. At such time, pump chamber 130-2 reduces in volume, causing the chamber 130-1 to fill with fluid received from fluid source 120-1 through check valve 125-1. Check valve 125-1 prevents fluid from flowing in a backward direction from diaphragm pump 130 to fluid source 120-1. Check valve 125-2 prevents fluid from flowing in a backward direction from conduit path 138 to the pump chamber 130-1.

Assume that prior to filling, the chamber 130-1 is substantially empty of fluid. In one embodiment, to draw fluid into chamber 130-1 with negative pressure from tank 170-2 as discussed above, the fluid flow manager 215-1 generates respective control signals V1 and V5 to open valve 160-1 and 160-5 (while all other valves are closed) to draw fluid from fluid source 120-1 and check valve 125-1 into chamber 130-1.

Subsequent to chamber 130-1 being filled with fluid, the fluid flow manager 215 controls settings of the valves 160 to apply a positive pressure from tank 170-1 to chamber 130-2 of diaphragm pump 130. For example, via generation of control signals V4 and V5, the fluid flow manager 215 opens valves 160-4 and 160-5 and closes all other valves.

In one embodiment, the control signal 230-1 generated by monitor resource 210 is an enable signal. The monitor resource 210 produces the enable signal when there are no detected failures conditions associated with the fluid delivery system 104. Electro mechanical converter 320-1 receives control signal 230-1 control signal 230-2 and produces a mechanical response controlling valve 160-5 to the appropriate opened or closed position. In one embodiment, the control signal 230-1 is a power signal produced by the power manager 191 but controlled by monitor resource 210. The monitor resource 210 produces control signal 230-1 such that a proper voltage is applied to power the electro-mechanical converter 320-1 to an ON state in certain instances. The monitor resource 210 produces the control signal 230-1 to depower (such as remove one or more voltage rails) the electro mechanical converter 320-1 in other instances. When control signal 230-1 is set to an enabled state, the control signal 230-2 produced by fluid flow manager 215-1 dictates whether valve 160-5 is set to an open or closed position. When control signal 230-1 is set to a disabled state (such as when the power signal is terminated to turn off or depower the electro mechanical converter 320-1), the control signal 230-2 produced by fluid flow manager 215-1 is unable to control a setting of valve 160-5 to an open or closed position. Instead, in this latter instance, the valve 160-5 is set to a default closed state, preventing delivery of fluid from fluid source 120-1 to recipient 108.

Conversely, when both valve 160-5 (in accordance with control signal 230-2 during a condition when the control signal 230-1 is set to the enabled state) and valve 160-4 are opened, the flow of gas from positive tank 170-1 to pump chamber 130-2 causes pumping of fluid from chamber 130-1 through check valve 125-2 along conduit path 138 to the target recipient 108. As previously discussed, during application of positive pressure of chamber 130-2, check valve 125-1 prevents fluid in chamber 130-1 from flowing back into fluid source 120-1.

As shown, the conduit path 138 through cassette 134 can include filter resource 112 that eliminates air and/or particulate matter in the fluid from being pumped to the target recipient 108.

Additionally conduit path 138 can include an in-line flow resistor 115. In one embodiment, the fluid flow manager 215 utilizes the in-line flow resistor as one means to control a rate of delivering fluid to the target recipient 108. For example, at a given driving pressure in chamber 130-2, to decrease a rate of flow, the fluid flow manager 215 increases a resistance of the in-line flow resistor 115. To increase a flow rate of fluid from the chamber 130-1 to the target recipient 108, the fluid flow manager 215 decreases a resistance of the in-line flow resistor 115.

Note that drive pressure in chamber 130-2 is another way to control a rate of delivering fluid to the target recipient 108. At a given position of an in-line flow resistor 115, the controller can use air pump 180 and pressure gauge 135-4 to set a target drive pressure in positive tank 170-1. That drive pressure can then be applied to pump chamber 130-2 (by opening valve 160-5) to drive the fluid in chamber 130-1 to target recipient 108. To increase a flow rate of fluid from the chamber 130-1 to the target recipient 108, the fluid flow manager 215 can be configured to increase the drive pressure in positive tank 170-1. To decrease a flow rate, the fluid flow manager 215 can be configured to decrease the drive pressure in positive tank 170-1.

Note that conduit path 138 also can include gas detector resource 110. The gas detector resource 110 can be configured to detect presence of air (or other gases) in the fluid being pumped through conduit path 138 to the target recipient 108. Based on feedback from the gas detector resource 110 as monitored by the fluid flow manager 215, the fluid flow manager 215 can be configured to notify monitor resource 210. In response to detecting this failure condition (detection of gas as indicated by the fluid flow manager 215), the monitor resource 210 initiates any suitable response as previously discussed such as activation of a respective alarm, terminating operation of the fluid delivery pumps 225, etc.

As previously discussed, one way to disable fluid delivery pumps 225-1 from continuing a respective infusion of fluid is to shut off valve 160-5. However, note that any other suitable action can be performed such as terminating power to one or more other valves. For example, if desired, the monitor resource 210 can be configured to cause valve 160-5 as well as valve 465 to open during a failure condition such that the pressure in chamber 130-2 of diaphragm pump 130 and chamber 150 equalizes to ambient pressure. In other words, the termination of powering of electromechanical converter 320-1 in accordance with control output produced by monitor resource 210 can result in the valve 160-5 being set to a corresponding default OPEN position. Additionally, in a manner as previously discussed, removal of power to a corresponding electro mechanical converter controlling a state of valve 465 can cause the valve 465 to default to a respective OPEN state. Thus, in accordance with one embodiment, termination of power to corresponding electromechanical converters associated with valve 160-5 and valve 465 can immediately cause both valves 160-5 in 465 to open, resulting in the diaphragm pump 130 discontinuing delivering fluid from fluid source 120-1 to recipient 108.

During a delivery phase, the fluid flow manager 215 can be configured to mainly apply pressure to chamber 130-2 with gas from tank 170-1 or tank 150 to cause the fluid in chamber 130-1 to be pumped to the target recipient 108. Delivery of the fluid in chamber 130-1 through conduit path 138 to target recipient 108 can be controlled by the fluid flow manager 215 in accordance with a pre-selected fluid delivery rate. In other words, the fluid flow manager 215 controls positive pressure applied chamber 130-1 to control a respective fluid flow rate. As further discussed below, embodiments herein can include at least temporarily discontinuing application of pressure to chamber 130-2 in order to perform a measurement of fluid remaining in chamber 130 1. As shown and discussed, discontinuing application of pressure to chamber 130-2 can at least temporarily reducing a pressure in chamber 130-2.

During a fluid delivery phase, the fluid flow manager 215 supplies a substantially constant pressure to the chamber 130-2. Because the membrane 127 is flexible, the pressure in chamber 130-2 exerts a force on the fluid in chamber 130-1. In general, via application of the appropriate pressure to chamber 130-2, the fluid flow manager 215 is able to fairly accurately pump the fluid at a desired flow rate. However, in certain situations, the delivery system 100 can be perturbed, resulting in errors in the flow rate. For example, as previously mentioned, the fluid source 120-1 may be squeezed, the elevation of fluid source 120-1 may change, etc. Any of these conditions can impact an accuracy of a desired fluid delivery rate.

Note that in addition to applying positive pressure to the pump chamber 130-2 during a fluid delivery phase, embodiments herein can include occasionally checking how much of the fluid drawn into the chamber 130-1 has been pumped towards the target recipient 108 through conduit path 138. This enables the fluid flow manager 215 to accurately determine the actual flow rate of fluid, even during times when the system conditions are perturbed.

More specifically, one way to measure a fluid delivery rate during a respective delivery phase is to repeatedly measure how much of the fluid in the chamber 130-1 has been pumped towards target recipient 108 on conduit path 138 at one or more MEASUREMENT times during the delivery phase. For example, the fluid flow manager 215 can initiate checking the volume of gas in chamber 130-2 over multiple sample times of a positive pressure delivery cycle. Because it is known how much gas is initially in the chamber 130-2 at the beginning of a delivery phase, and based on calculating how much gas is in chamber 130-2 at different times, etc., the fluid flow manager 215 (i.e., controller) is able to accurately measure a rate of pumping or delivering the fluid from fluid source 120-1 over conduit path 138 to the target recipient 108 in between times of filling the chamber 130-2. Thus, the fluid flow manager 215 is able to accurately measure fluid delivery in very small increments of time between successive cycles of refilling the chamber 130-1 with additional fluid.

In one embodiment, as previously discussed, the total volume of the diaphragm pump 120-1 including chamber 130-1, chamber 130-2 and conduit there between is a known quantity. One embodiment herein includes calculating how much fluid remains in chamber 130-1 based on knowing the volume of chamber 130-2. That is, the volume of the chamber 130-1 can be calculated by subtracting the volume of chamber 130-1 from the total volume of diaphragm pump 130. As discussed below, the volume of chamber 130-2 is initially an unknown quantity but is calculated based on pressure and estimated temperature.

Note that additional details of controlling delivery of one or more fluids to a corresponding recipient 108 are more fully discussed in related U.S. patent application Ser. No. 14/171,433 filed on Feb. 3, 2014 and U.S. patent application Ser. No. 14/171,435 filed on Feb. 3, 2014, the entire teachings of both of which are incorporated herein by this reference.

As previously discussed, the fluid flow manager 215 forwards the estimated fluid delivery information to monitor resource 210 for analysis. As previously discussed with respect to FIG. 3, the monitor resource 210 generates one or more control signals to terminate delivery of fluid in the event that the failure is detected.

Figure 5:
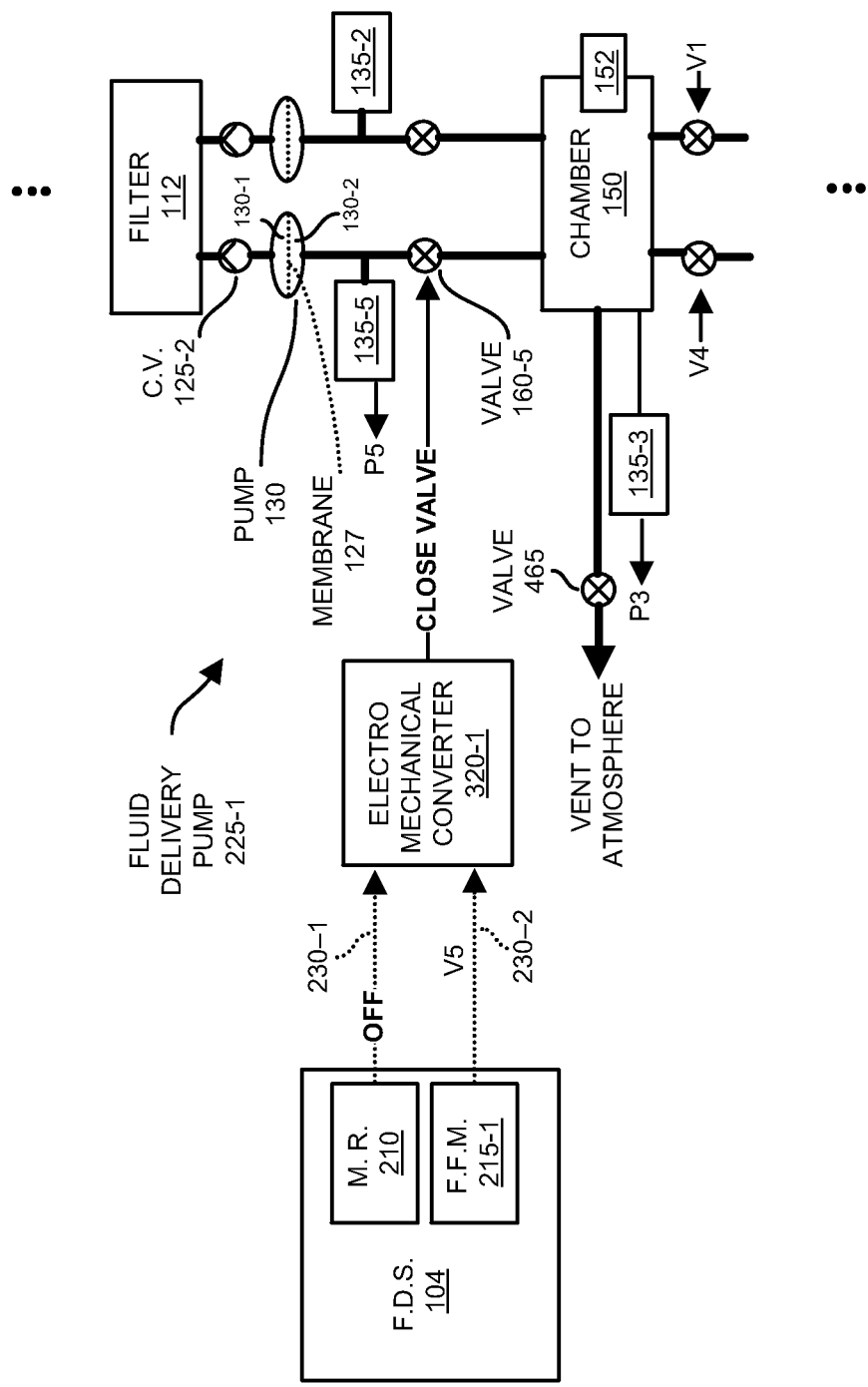
FIG. 5 is an example diagram illustrating deactivation of a respective fluid delivery pump according to embodiments herein.

FIG. 5 is an example diagram illustrating deactivation of a respective fluid delivery pump according to embodiments herein.

As previously discussed, the monitor resource 210 monitors the proper and safe operation of the fluid flow manager 215 and communication manager 220. In the event that an abnormal condition is detected in the flow-control domain such as that the fluid flow manager 215 indicates that delivery from fluid source 120-1 falls outside a respective acceptable delivery range 310 (previously discussed in FIG. 3), the monitor resource 210 initiates stopping the respective fluid flow. Additionally, the monitor resource 210 notifies the communication manager 220 of the event.

If the abnormal detected condition is severe (such as the condition that the patient's health is in danger), the monitor resource 210 stores an error code and deactivates the fluid delivery system 104. In certain instances, in accordance with one non-limiting example embodiment, the monitor resource 210 can be configured to prevent a respective caregiver 106 from using fluid delivery system 104 to deliver infusions if the monitor resource 210 produces one or more sufficiently severe error codes.

As previously discussed, when no failure is detected by the monitor resource 210, the monitor resource 210 sets control signal to the enabled state. While the control signal 230-1 is set to the enabled state, the control signal 230-2 produced by fluid flow manager dictates whether valve 160-5 is opened or closed. Accordingly, the fluid flow manager 215-1 produces control signal 230-2 to control a state of the valve 160-5 between open and closed positions to control the flow of fluid from the fluid delivery pump 225-1 to the recipient 108.

As previously discussed, the monitor resource 210 monitors one or more conditions to determine whether to disable the respective fluid delivery pump 225-1. Assume in this example that the monitor resource 210 detects that the delivery rate of fluid associated with fluid delivery pump 225-1 falls outside of the acceptable delivery rate range 310. In such an instance, the monitor resource 210 produces the control signal 230-1 to disable opening and closing the valve 160-5 via the control signal 230-2. For example, in one embodiment as mentioned, in response to detecting a failure condition, the monitor resource 210 sets the control signal 230-1 to the disable state. In such an instance, the electromechanical converter 320-1 causes the valve 160-5 to be set to an appropriate open or closed state. Accordingly, while the control signal 230-1 is set to the disabled state, the valve 160-5 is set to the appropriate state (such as the default closed state or open state), disabling the fluid flow manager 215-1 from controlling operations of the fluid delivery pump 225-1 and delivering fluid from source 120-1 to recipient 108.

Accordingly, the monitor resource 210 can be configured to receive input from the fluid flow manager 215-1 indicating an estimated volume of the fluid outputted from the fluid delivery pump 225-1 to the recipient 108 (as indicated in FIG. 3). In response to detecting that the estimated volume of the fluid delivered by the fluid delivery pump 225-1 deviates substantially (falls outside of the acceptable fluid rate delivery range 310) with respect to control settings as indicated by communication manager 220 (as received from caregiver 106 or information system 165), the monitor resource 210 produces the control signal 230-1 to open or close respective valve 160-5, preventing further flow of the fluid from source 120-1 to the recipient 108. Thus, the control signal 230-1 produced by the monitor resource 210 overrides control of the valve 160-5 with respect to control signal 230-2 produced by fluid flow manager 215-1.

In accordance with further embodiments, in the event that an abnormal condition associated with the communication manager 120 is detected, the monitor resource 210 terminates respective transmission and receipt of communications 126-1 and 126-2 over network 190.

In accordance with yet further embodiments, to prevent further delivery of fluid from fluid source 120-1 to a respective recipient 108, in response to detecting the failure condition, the monitor resource 210 can be configured to generate a respective control signal 230-1 to control generation or delivery of one or more voltage rails VR#1 to fluid delivery pump 225-1.

More specifically, one or more of the voltage rails VR#1 produced by the power supply 198-1 can be used to power the electromechanical converter 320-1. When the electromechanical converter 320-1 is powered by the one or more voltage rails VR#1 during normal operation, controller output from the fluid flow manager 215-1 controls a state of valve 160-5 via control signal 230-2. In other words, the control signal 230-2 controls whether the respective valve is OPEN or CLOSED when the electromechanical converter 320-1 is powered. During a respective failure condition as sensed by the monitor resource 210, the monitor resource 210 produces the control signal 230-1 to shut down powering of at least a portion of the fluid delivery system 104. In one embodiment, monitor resource 210 produces control signal 230-1 to terminate delivery of power (such as one or more voltages VR#1) to the respective electromechanical converter 320-1. In such an instance, the fluid flow manager 215-1 is no longer able to control the respective valve 160-5 via control signal 230-2 because the electromechanical converter 320-1 is depowered.

In one embodiment, when the electromechanical converter 320-1 is depowered (i.e., power removed), as previously discussed, the valve 160-5 defaults to a respective OPEN or CLOSED position that prevents further delivery of fluid to the corresponding recipient 108. In one embodiment, if desired, the valve 160-5 and valve 465 can be configured to default to a respective OPEN position when respective electromechanical converters are depowered. Thus, in one embodiment, upon detection of a respective failure condition, the removal of power caused by the monitor resource 210 results in a condition in which both valve 160-5 and valve 465 default to the OPEN position such that the chamber 130-2 of diaphragm pump 130 are vented to atmosphere. This prevents the diaphragm pump 130 from delivering fluid in chamber 130-12 the recipient 108.

Figure 6:
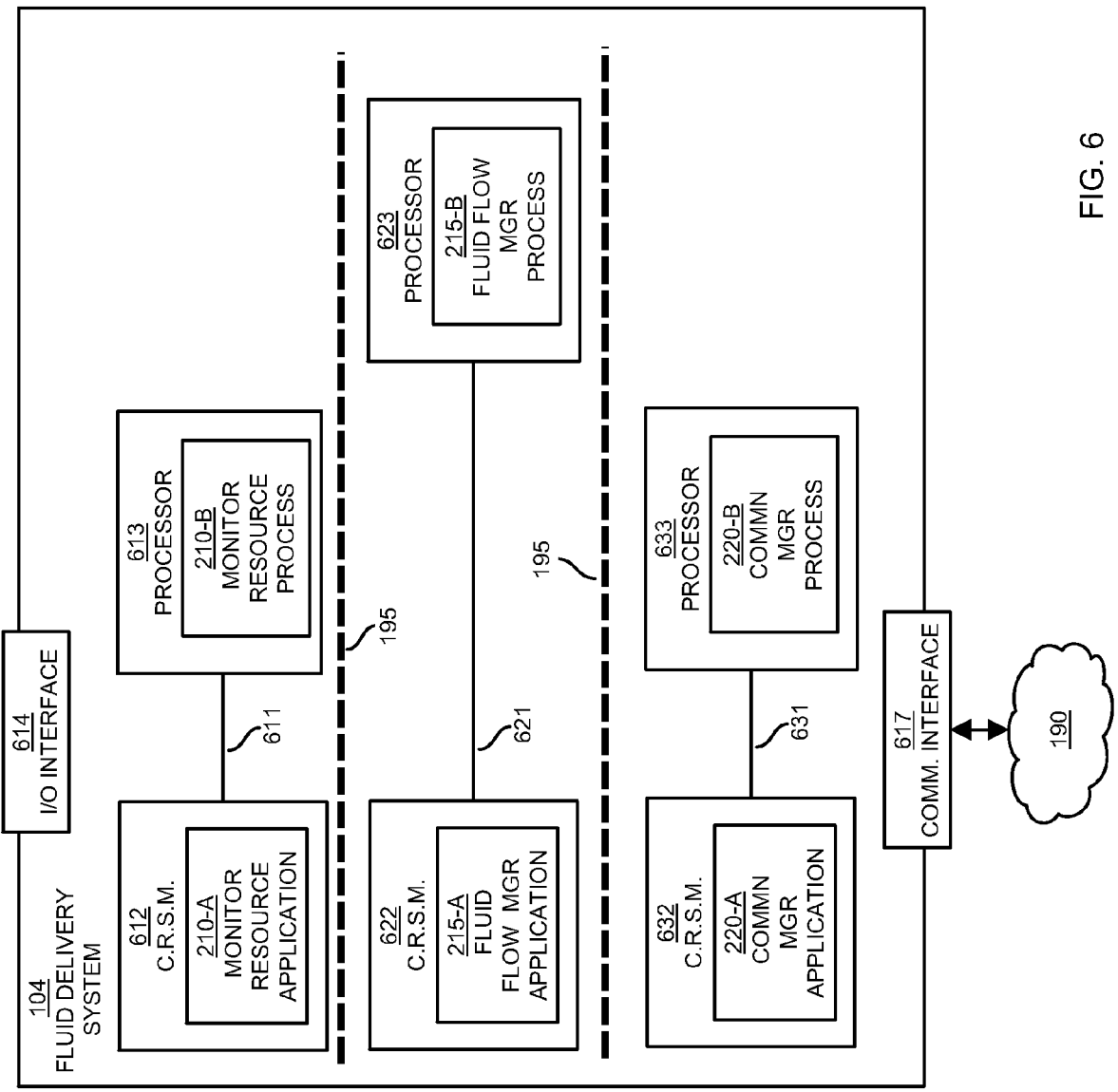
FIG. 6 is a diagram illustrating an example computer architecture in which to execute any of the functionality according to embodiments herein.

FIG. 6 is an example block diagram of a computer device for implementing any of the operations as discussed herein according to embodiments herein.

In one embodiment, fluid delivery system 104 includes one or more independently operating computer systems to execute monitor resource 210, fluid flow manager 215, communication manager 220, etc.

As shown, fluid delivery system 104 (a multiprocessor computer system) includes an interconnect 611, a processor 613 (such as one or more processor devices, computer processor hardware, etc.), computer readable storage medium 612 (such as hardware storage to store data), I/O interface 614, and communications interface 617.

Interconnect 611 provides connectivity amongst processor 613 and computer readable storage media 612. I/O interface 614 enables the monitor resource application 210-A (an instantiation of monitor resource 210) executing on processor 613 to produce output and receive input from other resources.

Computer readable storage medium 612 (i.e., computer readable hardware storage such as a non-transitory hardware medium) can be any hardware storage resource or device such as memory, optical storage, hard drive, rotating disk, etc. In one embodiment, the computer readable storage medium 612 stores instructions executed by processor 613.

As shown, computer readable storage media 612 is encoded with monitor resource application 210-A (e.g., software, firmware, etc.) executed by processor 613. Monitor resource application 210-A can be configured to include instructions to implement any of the operations associated with monitor resource 210 as discussed herein.

During operation of one embodiment, processor 613 (e.g., computer processor hardware) accesses computer readable storage media 612 via the use of interconnect 611 in order to launch, run, execute, interpret or otherwise perform the instructions in monitor resource application 210-A stored on computer readable storage media 612.

Execution of the monitor resource application 210-A produces processing functionality such as monitor resource process 210-B in processor 613. In other words, the monitor resource process 210-B associated with processor 613 represents one or more aspects of executing monitor resource application 210-A within or upon the processor 613 in the fluid delivery system 104.

As further shown, fluid delivery system 104 (a multiprocessor computer system) includes an interconnect 621, a processor 623 (such as one or more processor devices, computer processor hardware, etc.), computer readable storage media 622 (such as hardware storage to store data), I/O interface 614, and communications interface 617.

Interconnect 621 provides connectivity amongst processor 623 and computer readable storage media 622. I/O interface 614 enables the fluid flow manager 215 to produce output and receive input from other resources.

Computer readable storage medium 622 (i.e., computer readable hardware storage such as a non-transitory hardware medium) can be any hardware storage resource or device such as memory, optical storage, hard drive, rotating disk, etc. In one embodiment, the computer readable storage media 622 stores instructions executed by processor 623.

As shown, computer readable storage media 622 is encoded with fluid flow manager application 215-A (e.g., software, firmware, etc.) executed by processor 623. Fluid flow manager application 215-A can be configured to include instructions to implement any of the operations associated with fluid flow manager 215 as discussed herein.

During operation of one embodiment, processor 623 (e.g., computer processor hardware) accesses computer readable storage media 622 via the use of interconnect 621 in order to launch, run, execute, interpret or otherwise perform the instructions in the fluid flow manager application 215-A stored on computer readable storage media 622.

Execution of the fluid flow manager application 215-A produces processing functionality such as fluid flow manager process 215-B in processor 623. In other words, the fluid flow fluid flow manager process 215-B associated with processor 623 represents one or more aspects of executing fluid flow manager application 215-A within or upon the processor 623 in the fluid delivery system 104.

As further shown, fluid delivery system 104 (a multiprocessor computer system) includes an interconnect 631, a processor 633 (such as one or more processor devices, computer processor hardware, etc.), computer readable storage medium 632 (such as hardware storage to store data), I/O interface 614, and communications interface 617.

Interconnect 631 provides connectivity amongst processor 633, computer readable storage media 632, I/O interface 614, and communication interface 617.

I/O interface 614 provides connectivity to one or more repository and, if present, other devices such as a playback device, display screen, input resources, a computer mouse, etc.

Computer readable storage medium 632 (i.e., computer readable hardware storage such as a non-transitory hardware medium) can be any hardware storage resource or device such as memory, optical storage, hard drive, rotating disk, etc. In one embodiment, the computer readable storage medium 632 stores instructions executed by processor 633.

Communications interface 617 enables the communication manager 220 and processor 633 to communicate over a resource such as network 190 to retrieve information from remote sources and communicate with other computers. I/O interface 614 enables processor 613 to retrieve stored information from one or more repositories.

As shown, computer readable storage media 632 is encoded with communication manager application 220-A (e.g., software, firmware, etc.) executed by processor 633. Communication manager application 220-A can be configured to include instructions to implement any of the operations associated with communication manager 220 as discussed herein.

During operation of one embodiment, processor 633 (e.g., computer processor hardware) accesses computer readable storage media 632 via the use of interconnect 631 in order to launch, run, execute, interpret or otherwise perform the instructions in communication manager application 220-A stored on computer readable storage medium 632.

Execution of the communication manager application 220-A produces processing functionality such as communication manager process 220-B in processor 633. In other words, the communication manager process 220-B associated with processor 633 represents one or more aspects of executing communication manager application 220-A within or upon the processor 633 in the fluid delivery system 104.

As previously discussed, in one non-limiting example embodiment, the fluid delivery system 104 can include multiple communication interfaces that operate independently of each other as previously discussed. For example, in one embodiment, a first communication link facilitates communications between processor 613 and processor 633; a second communication interface facilitates communications between processor 633 and processor 623; a third communication interface facilitates communications between processor 623 and processor 613.

Those skilled in the art will understand that the fluid delivery system 104 (computer system) can include other processes and/or software and hardware components, such as an operating system that controls allocation and use of hardware resources to execute the functionality on different processors as discussed herein.

In accordance with different embodiments, note that computer system may be any of various types of devices, including, but not limited to, a wireless access point, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. In one non-limiting example embodiment, the computer system 850 resides in fluid delivery system 100. However, note that computer system 850 may reside at any location or can be included in any suitable resource in network environment 100 to implement functionality as discussed herein.

Functionality supported by the different resources will now be discussed via the flowchart in FIG. 7. Note that the steps in the flowcharts below can be executed in any suitable order.

Figure 7:
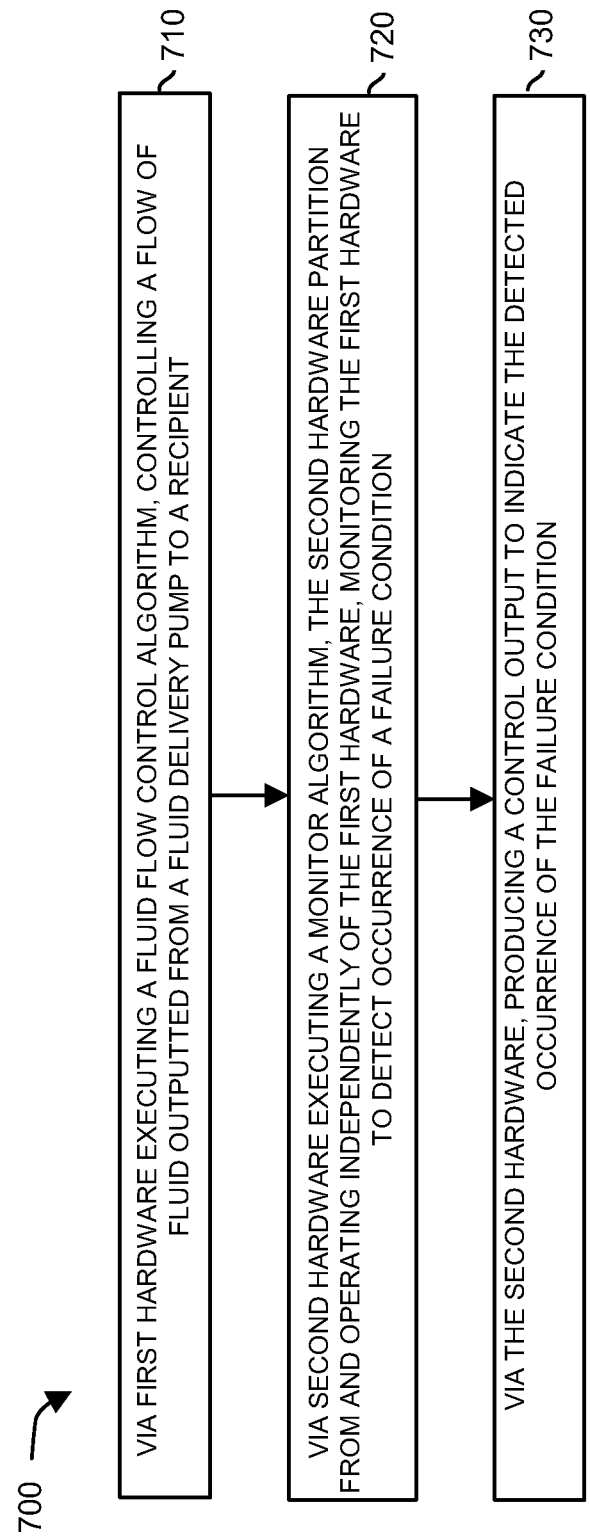
FIG. 7 are example diagrams illustrating a method according to embodiments herein.

FIG. 7 is a flowchart 700 illustrating an example method according to embodiments. Note that there will be some overlap with respect to concepts as discussed above.

In processing block 710, the fluid flow manager 215 (and corresponding first processor hardware) executes a fluid flow control algorithm to control a flow of fluid outputted from fluid delivery pump 225 to recipient 108.

In processing block 720, the monitor resource 210 (and corresponding second processor hardware operating independently of the first processor hardware) executes a monitor algorithm to detect occurrence of a failure condition.

In processing block 730, the monitor resource 210 produces a control output to indicate the detected occurrence of the failure condition.

Figure 8:
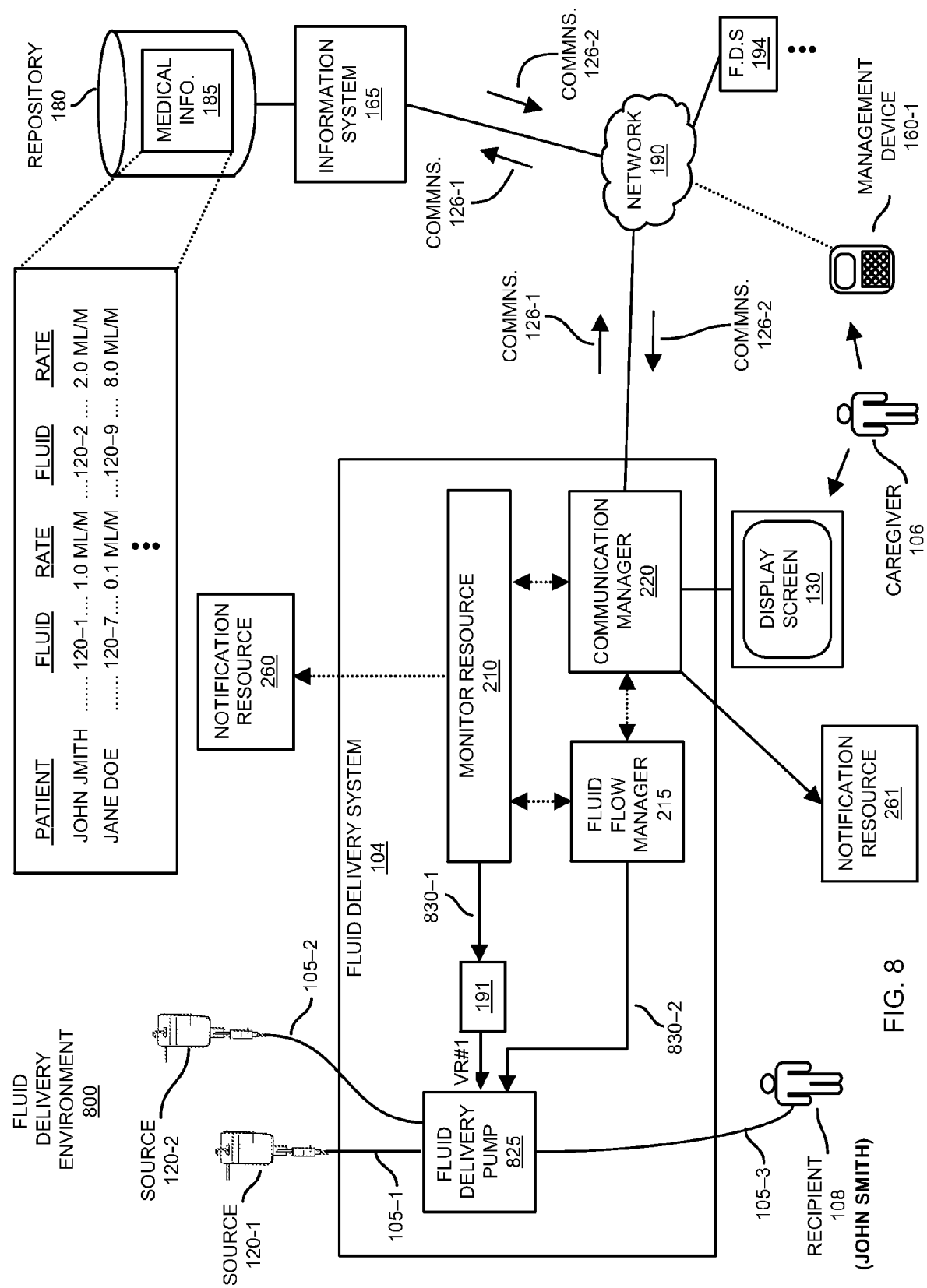
FIG. 8 is an example diagram illustrating functionality associated with a fluid delivery system according to embodiments herein.

FIG. 8 is an example diagram illustrating operational use of a respective fluid delivery system according to embodiments herein.

As previously discussed, one embodiment herein includes novel partitioning and segregation of hardware in a fluid delivery system 104 to perform different useful tasks. For example, as previously discussed, fluid delivery system 104 can include: fluid flow manager 215 (a first partitioning of hardware and/or software), monitor resource 210 (a second partitioning hardware and/or software), and communication manager 220 (a third partitioning of hardware and/or software).

In general, operation of the fluid delivery system 104 in fluid delivery environment 800 is similar to operation of the fluid delivery system 104 as operated in fluid delivery environment 200 as previously discussed. However, in this example embodiment, the fluid delivery system 104 operating in fluid delivery environment 800 includes a single fluid delivery pump 825 controlled by fluid flow manager 215 and monitor resource 210.

Communication manager 220 is communicatively coupled to one or more resources. In one embodiment, the fluid delivery system 104 includes display screen 130. Via display screen 130, the caregiver 106 is able to control operations associated with the fluid delivery system 104 and view delivery information. The display screen 130 displays a corresponding graphical user interface allowing the respective caregiver 106 to view information associated with delivering fluid and input control information to control delivering fluid in a desired manner. In one embodiment, input from the caregiver 106 (or other suitable resource) controls the programming and/or operation of the fluid delivery pump 825.

While the respective fluid flow manager 215 controls the fluid delivery pump 825 and a corresponding rate of delivering respective fluid to the recipient 108, the fluid flow manager 215 produces fluid delivery information such as data indicating an estimated volume of the fluid outputted from the respective fluid delivery pump 825 to the recipient 108. The fluid flow manager 215 forwards the delivery information to monitor resource 210 for analysis.

Figure 9:
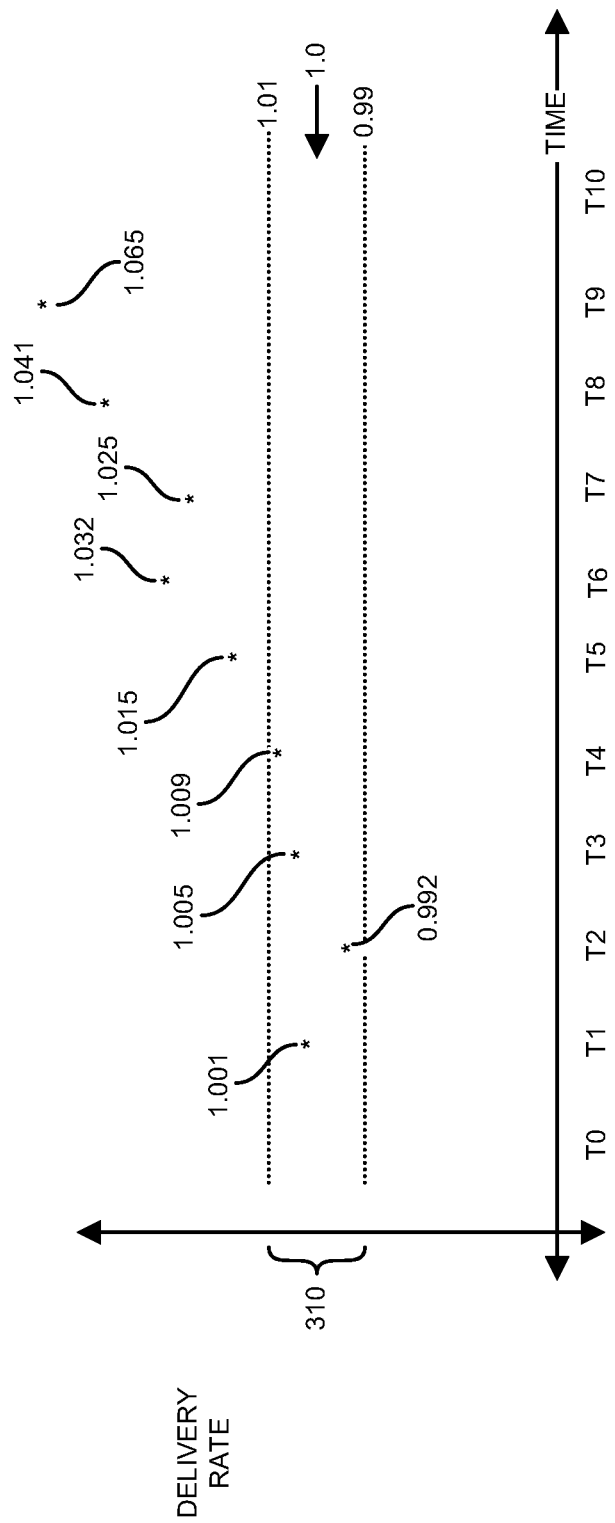
FIG. 9 is an example timing diagram illustrating an independently operating monitor resource monitoring delivery data received from a fluid flow manager according to embodiments herein.

The monitor resource 210 processes the received fluid delivery information received from the fluid delivery pump 825 and compares such information to acceptable delivery rate information as further shown in FIG. 9.

FIG. 9 is an example timing diagram illustrating analysis and monitoring of fluid delivery according to embodiments herein.

As previously discussed, initially, an appropriate entity such as the caregiver 106 or other suitable resource programs the fluid delivery system 104 to deliver fluid to a respective recipient 108. In response to programming, the communication manager 220 notifies the fluid flow manager 215 and the monitor resource 210 of the requested flow rate for delivery of one or more fluids. Once started, the fluid flow manager 215 sends the monitor resource 210 an indication of the current fluid flow delivery rate as provided by fluid delivery pump 825.

In one embodiment, the monitor resource 210 expects to receive fluid delivery feedback from the fluid flow manager 215 at a predetermined fixed rate or intervals. If the fluid flow manager 215 ceases to send updates of fluid flow delivery information to the monitor resource 210 at the expected update rate, the monitor resource 210 will initiate a system fault and shutdown the flow of fluids from any of one or more fluid source 120-1 and fluid source 120-2. Thus, in one embodiment, if the monitor resource 210 fails to receive updated flow information associated with the delivery pump 825 from the fluid flow manager 215, the monitor resource 210 will initiate shutting down the fluid delivery pump 825.

Additionally, if the difference between the actual flow rate (based on one or more flow updates as reported by the fluid flow manager 215 for one or more sample periods of the fluid delivery pump 825 delivering fluid to the recipient 108) falls outside expected limits such as range 310, the monitor resource 210 (safety processor) will initiate a system fault and shutdown the flow of fluids by fluid delivery pump 825 to the recipient 108.

In this example, the monitor resource 210 detects that fluid delivery pump 825 experiences a failure condition at or around time T5 and thereafter during which the fluid delivery pump 825 controlled by fluid flow manager 215 delivers an excess amount of fluid from fluid source 120-1 to recipient 108. In other words, at or around time T5 and thereafter, the monitor resource 210 receives feedback from the fluid flow manager 215 indicating that the fluid delivery pump 825 delivers an amount of fluid from fluid source 120-1 outside the range 310.

In response to detecting a failure condition such as that the estimated delivery rate for one or more fluid delivery cycles falls outside of the acceptable delivery range 310, the monitor resource 210 produces control output. The control output generated by the monitor resource 210 can be used to perform any suitable one or more functions. For example, in one embodiment the control output from the monitor resource 210 can be configured to perform operations such as: i) terminate delivery of the fluid in fluid source 120-1 by the fluid delivery pump 825 to the recipient 108, ii) provide notification (audible or visual indication) of the failure to a respective entity such as caregiver 106, etc.

The notified one or more entities (such as caregiver 106, one or more doctors, administrators of information system 165, etc.) receiving the failure notification initiated by monitor resource 210 then take appropriate measures to provide corrective action associated with the failing fluid delivery pump.

Figure 10:
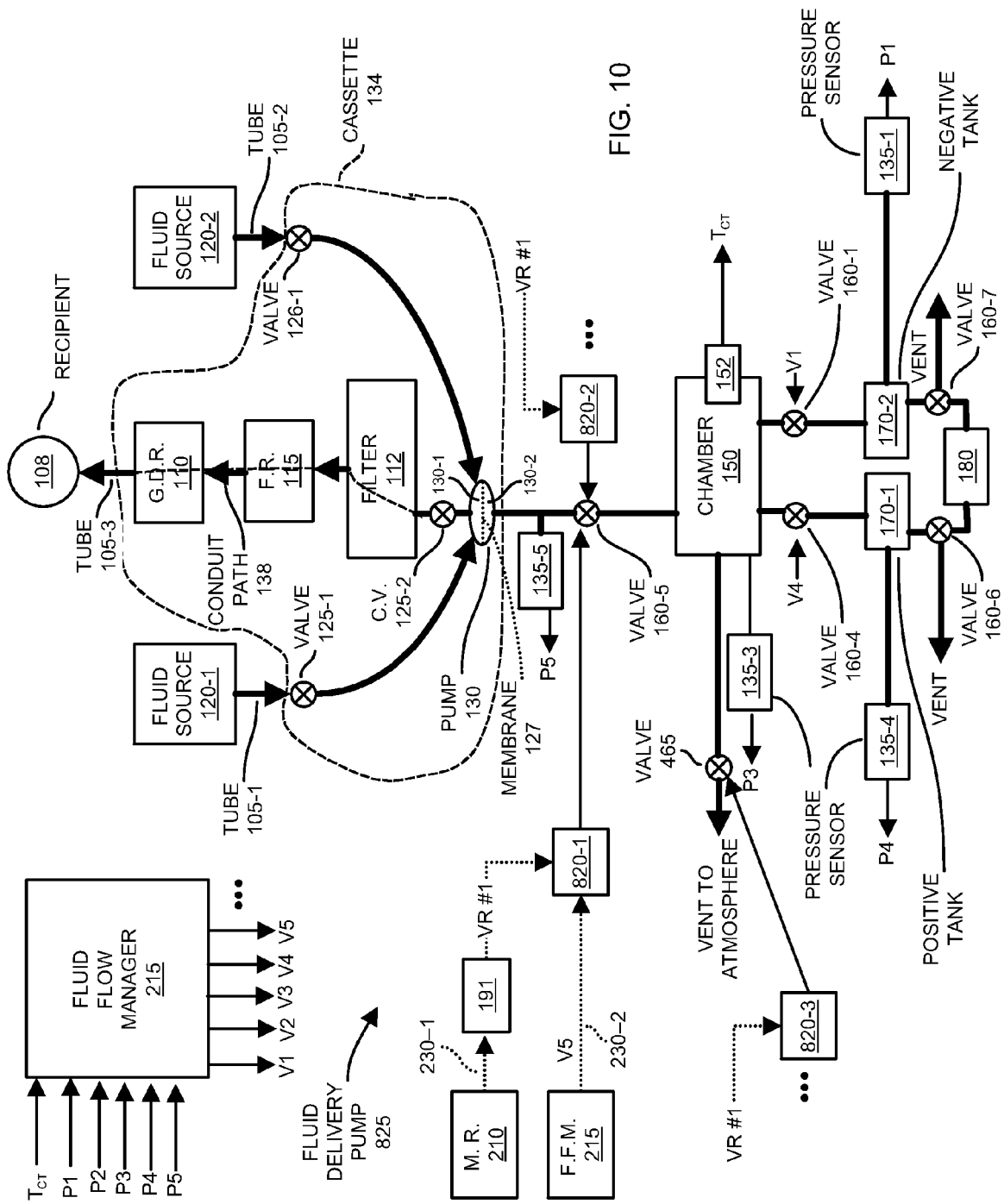
FIG. 10 is an example diagram illustrating a detailed operation of a fluid delivery pump according to embodiments herein.

FIG. 10 is an example diagram illustrating functional components and operation of a respective fluid delivery pump according to embodiments herein.

As shown, fluid delivery pump 825 includes appropriate components to facilitate delivery of fluid from one or more sources 120 (fluid source 120-1 and fluid source 120-2) to a respective recipient 108.

For example, fluid delivery pump 825 includes valve 125-1, valve 125-2, valve 126-1, diaphragm pump 130, pressure sensor 135-5, valve 160-5, gas detection resource 110, flow resistor 115, filter 112, chamber 150, pressure sensor 135-3, valve 465, temperature sensor 152, valve 160-4, valve 160-1, pressure sensor 135-4, positive tank 170-1, negative tank 170-2, pressure sensor 135-1, valve 160-6, valve 160-7, and air pump 180.

The fluid flow manager 215 of the fluid delivery system 104 controls operation of diaphragm pump 130 in disposable cassette 134 to precisely deliver fluid from one or more fluid sources such as fluid source 120-1 and fluid source 120-2 to a respective recipient 108.

In one embodiment, the fluid flow manager 215 controls the flow of fluid through the system 104 by adjustments to the drive pressure from the positive tank 170-1 and a variable hydraulic resistor (component such as fluid resistor 115) that is controlled by a motor or other suitable resource. Flow rate is measured using periodic volume calculations described below, and the control parameters are adjusted accordingly to drive the error between measured flow rate and target flow rate to zero.

Pump Cycle Overview

In accordance with yet further embodiments, a pump cycle associated with a respective diaphragm pump is defined as a motion of drawing fluid into chamber 130-1 of diaphragm pump 130 and then applying pressure to the complementary chamber 130-2 of diaphragm pump 130 to deliver the fluid to a recipient. In accordance with a specific non-limiting example embodiment, a pump cycle can be defined as at least partially moving of the membrane 127 in the diaphragm pump 130 from one extreme (such as "full" when chamber 130-1 is filled with fluid) to another extreme (such as "empty" when chamber 130-1 is emptied of fluid).

As shown in FIG. 4, membrane 127 divides the diaphragm pump 130 to include chamber 130-1 and chamber 130-2. Membrane 127 prevents fluid in chamber 130-1 from passing to chamber 130-2, and vice versa.

The membrane 127 dividing diaphragm pump 130 into chamber 130-1 and chamber 130-2 is flexible. When a negative pressure is applied to chamber 130-2, the volume of chamber 130-1 expands and draws fluid from fluid source 120-1 4 fluid source 120-2 into chamber 130-1.

The fluid flow manager 215 in this example selectively controls a state of valve 125-1 and valve 126-1 to select from which of one or more fluid sources 120 to draw fluid into chamber 130-one of diaphragm pump 130. Assume in this example embodiment that the fluid flow manager 214 opens valve 125-1 (while valve 126-1 is close), allowing fluid from fluid source 120-1 to be drawn into chamber 130-1 of diaphragm pump 130. After the fluid is drawn into the chamber 130-1, the fluid flow manager 215 closes the respective valve 125-1.

Subsequently, when a positive pressure is applied to chamber 130-2, the volume of fluid in chamber 130-1 decreases as a result of expelling the fluid from chamber 130-1 downstream through conduit path 138 to a respective recipient 108.

In one embodiment, the total volume or capacity of chamber 130-1 and chamber 130-2 is substantially constant regardless of the position of the membrane 127. Based on knowing the volume of fluid in chamber 130-2, the fluid flow manager 215 is able to determine a corresponding volume of fluid in chamber 130-1. For example, if the total volume of the diaphragm pump 130 is Vtotal, and the volume of chamber 130-2 is V2, the fluid delivery system 100 can determine the volume of chamber 130-1 by subtracting V2 from Vtotal.

Assume that prior to filling, the chamber 130-1 is substantially empty of fluid. In one embodiment, to draw fluid into chamber 130-1 with negative pressure from tank 170-2 as discussed above, the fluid flow manager 215 generates respective control signals to open valve 160-1, 160-5, and 125-1 (while all other valves are closed) to draw fluid from fluid source 120-1 into chamber 130-1.

Subsequent to chamber 130-1 being filled with fluid, the fluid flow manager 215 controls settings of the valves 160 to apply a positive pressure from tank 170-1 to chamber 130-2 of diaphragm pump 130. For example, via generation of appropriate control signals, the fluid flow manager 215 opens valves 125-2, 160-4, and 160-5 while all other valves are closed.

As previously discussed, assume that the monitor resource 210 detects occurrence of a failure condition in which the fluid flow manager 215 indicates that the fluid delivery pump 225 delivers fluid from fluid source 120-1 at an improper rate. By way of non-limiting example embodiment, in response to detecting this failure condition, fluid flow manager 210 generates a respective control signal and forwards it to power manager 191. The generated control signal notifies the power manager 191 to discontinue powering the electro mechanical converter 820-1. Because the electro mechanical converter 820-1 is depowered, the valve 125-2 defaults to a corresponding closed position, preventing further flow of any fluid in chamber 130-1 along the conduit path 138 to the recipient 108.

Additionally or alternatively, the monitor resource can be configured to shut down control to one or more additional valves such as valve 160-5 and valve 465. In a manner as previously discussed, valve 160-5 and valve 465 can be configured to default to a respective open state when power to a respective electro mechanical converter is terminated. For example, in one embodiment, the monitor resource 210 can be configured to depower electro mechanical converter 820-2, causing the respective valve 160-5 to defaults to a respective open state. Additionally, the monitor resource 210 can be configured to depower electro-mechanical converter 820-3, causing the respective valve 465 to default to a respective open state as well.

Controlling the valve 160-5 and valve 465 to respective open states vents any respective gases in chamber 150 to atmosphere. This removes any applied pressure to chamber 130-2 of diaphragm pump 130, terminating delivery of fluid in chamber 130-1 along conduit path 138 to recipient 108.

While one or more of the electro mechanical converters 820 are depowered in accordance with control signals generated by the monitor resource 210, any respective control signals produced by the fluid flow manager 215 will be unable to control the respective valves.

Accordingly, detection of a respective failure condition by the monitor resource 210 can be configured to cause the monitor resource 210 to control one or more valves in the fluid delivery pump 825 to a respective safe state, preventing further delivery of fluid.

Referring again to FIG. 8, note that each of the monitor resource 210, fluid flow manager 215, and communication manager 220 can be configured to monitor each other's health. For example, each of the resources (monitor resource 210, fluid flow manager 250, and communication manager 220) includes a respective watchdog circuit and algorithm (executable computer instructions) to monitor external circuitry.

The fluid flow manager 215 can be configured to monitor receipt of a respective heartbeat signal (such as generated every millisecond) from the monitor resource 210 and receipt of a respective heartbeat signal (such as generated every millisecond) from the communication manager 220. In one embodiment, if the fluid flow manager 215 fails to receive heartbeat signals from the monitor resource 210 (indicating that the fluid flow manager 215 has failed), but continues to receive proper heartbeat signals from the communication manager 220 (indicating that the communication manager 220 is still healthy), the fluid flow manager 215 continues to deliver fluid in accordance with previously received flow control commands.

If the fluid flow manager 215 receives proper heartbeat signals from the monitor resource 210 (indicating that the monitor resource 210 is still healthy), but fails to receive proper heartbeat signals from the communication manager 220 (indicating that the communication manager 220 has failed), the fluid flow manager 215 also continues to deliver fluid in accordance with previously received flow control commands.

If the fluid flow manager 215 fails to receive heartbeat signals from the monitor resource 210 and also fails to receive proper heartbeat signals from the communication manager 220 (indicating that both the monitor resource 210 and the communication manager 220 have both failed), the fluid flow manager 215 terminates delivery of as specified by previously received flow control commands. Accordingly, certain error conditions will result in portions of the fluid delivery system 104 shutting down. Other error conditions result in continued operation of the fluid delivery system 104.

Note again that techniques herein are well suited for use in management of fluid delivery systems. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A system comprising:
   first hardware, the first hardware controlling a fluid delivery pump, the first hardware controlling the fluid delivery pump to control a flow of fluid outputted from the fluid delivery pump to a recipient;
   second hardware partitioned from and operating independently of the first hardware, the second hardware in communication with the first hardware;
   third hardware, the third hardware partitioned from and operating independently of the first hardware and the second hardware, the third hardware operable to communicate control settings to both the first hardware and the second hardware, the first hardware operable to control the fluid delivery pump to deliver the fluid to the recipient as indicated by the control settings;
   the second hardware further operable to monitor feedback from the first hardware to verify delivery of the fluid in a manner as specified by the control settings received from the third hardware;
   wherein the feedback from the first hardware indicates an estimated volume of the fluid outputted from the fluid delivery pump to the recipient, the second hardware producing a control output to prevent further flow of the fluid to the recipient in response to detecting that the estimated volume of the fluid deviates with respect to the control settings as indicated by the third hardware; and
   wherein the second hardware produces the control output to control a state of a respective valve associated with the fluid delivery pump to terminate the flow of fluid from the fluid delivery pump to the recipient.

2. The system as in claim 1, wherein the respective valve is disposed in the fluid delivery pump; and
   wherein the control output produced by the second hardware controls the state of the respective valve to prevent further flow of the fluid to the recipient in response to detecting that the fluid delivered by the fluid delivery pump falls outside an acceptable fluid delivery range.

3. The system as in claim 2, wherein the control output produced by the second hardware overrides control of the respective valve by the first hardware.

4. The system as in claim 1, wherein the first hardware executes a first set of software instructions to control the fluid delivery pump and the flow of fluid;
   wherein the second hardware executes a second set of software instructions to monitor the first hardware; and
   wherein the third hardware executes a third set of software instructions to support communications with a remote server to retrieve the control settings.

5. The system as in claim 1 further comprising:
   a communication interface, the communication interface facilitating conveyance of communications between the first hardware and the second hardware.

6. The system as in claim 1 further comprising:
   a first communication interface, the first communication interface facilitating conveyance of communications between the first hardware and the second hardware; and a second communication interface, the second communication interface facilitating conveyance of communications between the second hardware and the third hardware; and a third communication interface, the third communication interface facilitating conveyance of communications between the first hardware and the third hardware.

7. The system as in claim 6 further comprising:

a communication link extending between the third hardware and a remote network, the communication link conveying communications associated with the fluid delivery pump.

8. The system as in claim 6 further comprising:

a display screen communicatively coupled to the third hardware, the third hardware initiating display of configuration information associated with the fluid delivery pump on the display screen for viewing by a caregiver operating the fluid delivery pump.

9. The system as in claim 1 further comprising:

a notification interface, the third hardware operable to control the notification interface to notify a respective caregiver operating the fluid delivery pump of an occurrence of a fluid delivery failure condition, the third hardware operable to receive notification of the fluid delivery failure condition from the second hardware.

10. The system as in claim 1 further comprising:

a first communication link, the third hardware in communication with the first hardware over the first communication link;

a second communication link operating independently of the first communication link, the third hardware in communication with the second hardware over the second communication link; and a third communication link operating independently of the second communication link and the first communication link, the second hardware in communication with the first hardware over the third communication link.

11. The system as in claim 10, wherein the third hardware is operable to communicate the control settings to the first hardware over the first communication link;

wherein the third hardware is operable to communicate the control settings to the second hardware over the second communication link; and wherein the first hardware is operable to communicate the feedback to the second hardware over the third communication link.

12. The system as in claim 1 further comprising:

a power manager operable to power each of the first hardware, the second hardware, and the third hardware with a different power source.

13. The system as in claim 1, wherein the third hardware is operable to control a display screen to provide notification of a failure condition; and wherein the third hardware is operable to provide notification of the failure condition to a remote server over a network.

14. The system as in claim 1, wherein the second hardware is in communication with the first hardware to determine an estimated rate of the fluid outputted from the fluid delivery pump to the recipient based on the feedback, the second hardware producing the control output to stop the flow of fluid from the fluid delivery pump in response to detecting that the estimated rate of the fluid falls outside of an acceptable delivery range.

* * * * *

UNITED STATES PATENT AND TRADEMARK OFFICE
CERTIFICATE OF CORRECTION

PATENT NO. : 9,849,232 B2  
APPLICATION NO. : 14/494803  
DATED : December 26, 2017  
INVENTOR(S) : George W. Gray et al.

Page 1 of 1

It is certified that error appears in the above-identified patent and that said Letters Patent is hereby corrected as shown below:

On the Title Page

Item (73) Under Assignee, Invenix, Inc. should read --Ivenix, Inc.--

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*